(12) United States Patent
Akiyama et al.

(10) Patent No.: US 7,674,611 B2
(45) Date of Patent: Mar. 9, 2010

(54) MODIFIED ETHYLENEDIAMINE-N, N'-DISUCCINATE: ETHYLENEDIAMINE LYASE

(75) Inventors: Takanori Akiyama, Kanagawa (JP); Wataru Mizunashi, Kanagawa (JP); Tetsuji Nakamura, Kanagawa (JP)

(73) Assignee: Mitsubishi Rayon Co., Ltd (JP)

( * ) Notice: Subject to any disclaimer, the term of this patent is extended or adjusted under 35 U.S.C. 154(b) by 0 days.

(21) Appl. No.: 11/569,339

(22) PCT Filed: May 20, 2004

(86) PCT No.: PCT/JP2004/007226

§ 371 (c)(1),
(2), (4) Date: Jan. 10, 2007

(87) PCT Pub. No.: WO2005/113766

PCT Pub. Date: Dec. 1, 2005

(65) Prior Publication Data

US 2008/0009053 A1 Jan. 10, 2008

(51) Int. Cl.
- C12N 9/88 (2006.01)
- C12P 13/00 (2006.01)
- C07H 21/04 (2006.01)

(52) U.S. Cl. .................. 435/232; 435/128; 536/23.2

(58) Field of Classification Search ............... 435/232, 435/69.1, 252.3, 128; 536/23.2
See application file for complete search history.

(56) References Cited

U.S. PATENT DOCUMENTS 6,168,940 B1  1/2001  Mizunashi et al.

6,503,739 B1  1/2003  Kaneko et al.

FOREIGN PATENT DOCUMENTS

| EP | 0 845 536 A2 | 6/1998 |
|---|---|---|
| EP | 0 927 762 A2 | 7/1999 |
| EP | 1043400 | 10/2000 |
| EP | 1174515 | 1/2002 |
| WO | WO-02/06442 A2 | 1/2002 |

OTHER PUBLICATIONS

Branden et al. Introduction to protein structure, Gerald Publishing Inc., New York, p. 247, 1991.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Seffernick et al. Melamine deaminase and atrazine chlorohydrolase: 98 percent identical but functionally different, J Bacteriol. Apr. 2001;183(8):2405-10.*
International Search Report for PCT/JP2004/007226 mailed Jul. 6, 2004.
"Random-priming in vitro recombination: an effective tool for directed evolution" by Shao et al., Nucleic Acids Research, 1998, vol. 26, No. 2, pp. 681-683.
"Directed evolution of a thermostable esterase" by Giver et al., Proc. Natl. Acad. Sci. USA, vol. 95, pp. 12809-12813, Oct. 1998.
Segers et al., Intl. J. Syst. Bacteriol., 1994, vol. 44, No. 3, p. 499-510.

* cited by examiner

*Primary Examiner*—Richard Hutson
*Assistant Examiner*—Iqbal H Chowdhury
(74) *Attorney, Agent, or Firm*—Darby & Darby, P.C.

(57) ABSTRACT

The present invention provides a modified ethylenediamine-N,N'-disuccinate:ethylenediamine lyase. The present invention also provides a protein that comprises the amino acid sequence represented by SEQ ID NO: 1; or a protein that comprises an amino acid sequence derived from the amino acid sequence represented by SEQ ID NO: 1 by deletion, substitution, or addition of one or more amino acid residues, and has an ethylenediamine-N,N'-disuccinate:ethylenediamine lyase activity.

12 Claims, 7 Drawing Sheets

```
                          SEQUENCE LISTING

<160> NUMBER OF SEQ ID NOS: 6

<210> SEQ ID NO 1
<211> LENGTH: 495
<212> TYPE: PRT
<213> ORGANISM: Brevundimonas diminuta
<220> FEATURE:
<221> NAME/KEY: VARIANT
<222> LOCATION: 1
<223> OTHER INFORMATION: Xaa is Met or is absent

<400> SEQUENCE: 1

Xaa Thr Pro His Asn Pro Asp Ala Thr Arg Ile Gly Arg Ala Ser Gly
 1               5                  10                  15

Ala Lys Ala Pro Glu Phe Gln Glu Leu Tyr Asp Phe Glu Ala Ala Ala
            20                  25                  30

Leu Thr Leu Thr Ser Ala Val Phe Pro Tyr Asp Ser Lys Ile His Arg
        35                  40                  45

Ala His Val Val Met Leu Ala Glu Gln Asp Ile Leu Thr Arg Asp Glu
    50                  55                  60

Ala Ala Ser Ile Leu Asn Gly Leu Ala Lys Ala Asp Glu Leu Ala Gly
65                  70                  75                  80

Lys Asp Ala Ala Leu Arg Thr Tyr Leu Pro Tyr Glu Ala Ala Leu Lys
                85                  90                  95

Arg Glu Ile Gly Ser Val Ala Gly Lys Met His Ile Gly Arg Ser Arg
            100                 105                 110

Asn Asp Leu Ala Asn Ala Gly Lys Arg Met Phe Leu Arg Asp Gln Leu
        115                 120                 125

Leu Arg Thr Val Glu Ala Val Ile Ala Leu Arg Glu Ala Val Val Thr
    130                 135                 140

Lys Ala Ala Asp His Leu Asp Thr Val Met Val Val Tyr Thr Gln Arg
145                 150                 155                 160

Lys Glu Ala Gln Pro Ile Thr Leu Gly His Tyr Leu Met Ala Ile Ser
                165                 170                 175

Glu Asn Leu Gly Lys Asn Leu Ala Arg Tyr Arg Glu Leu His Pro Arg
            180                 185                 190

Ile Asn Gln Cys Pro Leu Gly Ala Ala Ala Thr Ala Gly Thr Gly Trp
        195                 200                 205

Pro Leu Asp Arg Asp Arg Thr Ala Ala Leu Leu Gly Phe His Gly Leu
    210                 215                 220

Val Val Asn Ser Ile Glu Gly Val Ala Gly Trp Asp His Val Ala Glu
225                 230                 235                 240

Phe Ala Phe Asp Asn Ala Val Phe Leu Ser Gly Leu Ser Arg Leu Ala
```

```
                      245                 250                 255
Ser Glu Ile Gln Leu Trp Ser Thr Asp Glu Tyr Gln Met Ala Glu Leu
            260                 265                 270

Asp Ser Ala Phe Ala Gly Thr Ser Ser Ile Met Pro Gln Lys Lys Asn
        275                 280                 285

Pro Asp Ser Leu Glu Arg Ser Arg Lys Ala Ala Phe Ala Ala Met Gly
    290                 295                 300

Pro Leu Val Ala Ile Leu Thr Ser Leu Asn Gly Ile Glu Tyr Gln Tyr
305                 310                 315                 320

Ser Ala Ala Arg Val Glu Leu Glu Pro Arg Ser Ile Asp Ala Leu Ile
                325                 330                 335

Ala Ala Thr His Ala Met Thr Gly Val Val Arg Thr Leu His Pro Asn
            340                 345                 350

Lys Glu Gln Met Leu Arg Tyr Ala Ala Glu Asn Tyr Ala Thr Met Thr
        355                 360                 365

Asp Leu Thr Asp Leu Leu Val Arg Arg Ile Gly Ile Asp Tyr Arg Glu
    370                 375                 380

Ala His Glu Ile Val Ala Arg Val Val Met Thr Ala Ile Glu Arg Gly
385                 390                 395                 400

Ile Lys Ala Asn Ala Ile Gly Leu Asp Leu Val Gln Glu Ala Ala Val
                405                 410                 415

Ala Gln Thr Gly Asn Arg Ile Glu Ile Gly Ala Ala Asp Ile Ala Asp
            420                 425                 430

Ala Leu Asp Pro Val Gln Asn Val Ala Arg Arg Lys Gly Arg Gly Met
        435                 440                 445

Pro Ala Pro Glu Ser Val Arg Ala Ala Ile Ala Glu Ala Arg Gln Glu
    450                 455                 460

Leu Asp Ala Asp Lys Ala Trp Leu Glu Asp Arg Arg Ala Gly Leu Ala
465                 470                 475                 480

Asp Ala Asp Ala Ala Leu Glu Glu Ala Val Ala Gly Ile Thr Thr
                485                 490                 495

<210> SEQ ID NO 2
<211> LENGTH: 1488
<212> TYPE: DNA
<213> ORGANISM: Brevundimonas diminuta
<220> FEATURE:
<221> NAME/KEY: CDS
<222> LOCATION: (1)..(1485)

<400> SEQUENCE: 2 atg acc ccg cat aac cca gat gcc acc cgt atc ggc cgt gcc agc ggc    48
Met Thr Pro His Asn Pro Asp Ala Thr Arg Ile Gly Arg Ala Ser Gly
  1               5                  10                  15 gcg aag gcg ccg gaa ttc cag gaa ctc tat gac ttc gaa gca gcg gca    96
Ala Lys Ala Pro Glu Phe Gln Glu Leu Tyr Asp Phe Glu Ala Ala Ala
                 20                  25                  30 ctc acc ctg acg agc gcc gtc ttt cct tac gac agc aag att cat cgt   144
Leu Thr Leu Thr Ser Ala Val Phe Pro Tyr Asp Ser Lys Ile His Arg
             35                  40                  45 gct cac gtc gtc atg ctg gct gaa cag gac atc ctg acc cgg gac gag   192
Ala His Val Val Met Leu Ala Glu Gln Asp Ile Leu Thr Arg Asp Glu
         50                  55                  60 gct gcc agc atc ctg aac ggg ctg gcc aag gcg gat gaa ctg gcg gga   240
Ala Ala Ser Ile Leu Asn Gly Leu Ala Lys Ala Asp Glu Leu Ala Gly
 65                  70                  75                  80 aag gac gcg gcg ctg cgc acc tac ctg ccc tat gag gcc gcg ctg aaa   288
Lys Asp Ala Ala Leu Arg Thr Tyr Leu Pro Tyr Glu Ala Ala Leu Lys
```

```
               Lys Asp Ala Ala Leu Arg Thr Tyr Leu Pro Tyr Glu Ala Ala Leu Lys
                               85                  90                  95 cgc gag atc ggc tcc gtt gcc ggg aag atg cat atc ggg cgc agt cgc              336
Arg Glu Ile Gly Ser Val Ala Gly Lys Met His Ile Gly Arg Ser Arg
                100                 105                 110 aac gac ctc gcc aat gcc ggt aaa cgc atg ttc ctg cgt gac cag ctg              384
Asn Asp Leu Ala Asn Ala Gly Lys Arg Met Phe Leu Arg Asp Gln Leu
            115                 120                 125 ctg cgc acc gtc gag gct gtg atc gca ttg cgc gag gca gtc gtg acc              432
Leu Arg Thr Val Glu Ala Val Ile Ala Leu Arg Glu Ala Val Val Thr
        130                 135                 140 aag gcc gcc gac cat ctc gac acg gtg atg gtc gtc tac acc cag cgc              480
Lys Ala Ala Asp His Leu Asp Thr Val Met Val Val Tyr Thr Gln Arg
145                 150                 155                 160 aag gag gcc cag ccg atc acg ctc ggc cat tac cta atg gcg atc agc              528
Lys Glu Ala Gln Pro Ile Thr Leu Gly His Tyr Leu Met Ala Ile Ser
                165                 170                 175 gaa aat ctg ggc aag aac ctc gcc cgc tat cgc gag ctc cat ccg cgc              576
Glu Asn Leu Gly Lys Asn Leu Ala Arg Tyr Arg Glu Leu His Pro Arg
            180                 185                 190 atc aac caa tgt ccc ctc ggc gcc gct gcc acg gcg ggc acg ggc tgg              624
Ile Asn Gln Cys Pro Leu Gly Ala Ala Ala Thr Ala Gly Thr Gly Trp
        195                 200                 205 ccg ctg gat cgc gac cgc acc gca gca ctg ctg ggt ttc cac ggg ctc              672
Pro Leu Asp Arg Asp Arg Thr Ala Ala Leu Leu Gly Phe His Gly Leu
210                 215                 220 gtc gtc aac agc atc gag ggc gtg gcc ggc tgg gac cac gtc gcg gaa              720
Val Val Asn Ser Ile Glu Gly Val Ala Gly Trp Asp His Val Ala Glu
225                 230                 235                 240 ttc gcc ttc gac aat gcc gtc ttc ctg agc ggc ctc agc cgc ctg gct              768
Phe Ala Phe Asp Asn Ala Val Phe Leu Ser Gly Leu Ser Arg Leu Ala
                245                 250                 255 tcc gag atc cag ctc tgg agc acg gac gag tat cag atg gcg gaa ctc              816
Ser Glu Ile Gln Leu Trp Ser Thr Asp Glu Tyr Gln Met Ala Glu Leu
            260                 265                 270 gac tcc gcc ttc gcc ggc acc agc agc atc atg ccg cag aag aaa aac              864
Asp Ser Ala Phe Ala Gly Thr Ser Ser Ile Met Pro Gln Lys Lys Asn
        275                 280                 285 ccg gat tcg ctg gag cgc agc cgg aag gcc gcc ttc gcg gcg atg ggg              912
Pro Asp Ser Leu Glu Arg Ser Arg Lys Ala Ala Phe Ala Ala Met Gly
290                 295                 300 ccg ctg gtc gcc atc ctc acc tct ctc aat ggt atc gag tac cag tac              960
Pro Leu Val Ala Ile Leu Thr Ser Leu Asn Gly Ile Glu Tyr Gln Tyr
305                 310                 315                 320 agc gcc gcc agg gtc gag ctc gaa ccg cga tcc atc gat gcg ctg atc             1008
Ser Ala Ala Arg Val Glu Leu Glu Pro Arg Ser Ile Asp Ala Leu Ile
                325                 330                 335 gcg gcc acc cac gcg atg acg ggc gtc gtg cgg acg ctt cat ccc aac             1056
Ala Ala Thr His Ala Met Thr Gly Val Val Arg Thr Leu His Pro Asn
            340                 345                 350 aag gag cag atg ctg cgc tat gcg gca gag aac tac gcc acc atg acc             1104
Lys Glu Gln Met Leu Arg Tyr Ala Ala Glu Asn Tyr Ala Thr Met Thr
        355                 360                 365 gac ctg acc gac ctg ctc gtc cgt cgc atc ggc atc gac tat cgc gag             1152
Asp Leu Thr Asp Leu Leu Val Arg Arg Ile Gly Ile Asp Tyr Arg Glu
370                 375                 380 gcc cat gag atc gtg gcg cgc gtg gtg atg acg gcg atc gag cgc ggc             1200
Ala His Glu Ile Val Ala Arg Val Val Met Thr Ala Ile Glu Arg Gly
385                 390                 395                 400
```

-continued

| | | | | | | | | | | | | | | |
|---|---|---|---|---|---|---|---|---|---|---|---|---|---|---|
| atc | aag | gcc | aac | gcc | atc | gga | ctg | gac | ctc | gtg | cag | gag | gcc | gcg | gtc | 1248 |
| Ile | Lys | Ala | Asn | Ala | Ile | Gly | Leu | Asp | Leu | Val | Gln | Glu | Ala | Ala | Val |
| | | | | 405 | | | | | 410 | | | | | 415 | |

| gcg | cag | acg | ggc | aac | cgg | atc | gag | atc | ggt | gcg | gcc | gac | atc | gcc | gat | 1296 |
| Ala | Gln | Thr | Gly | Asn | Arg | Ile | Glu | Ile | Gly | Ala | Ala | Asp | Ile | Ala | Asp |
| | | | 420 | | | | | 425 | | | | | 430 | | |

| gcg | ctc | gat | ccg | gtt | cag | aac | gtc | gcc | cgt | cgc | aag | ggc | agg | ggc | atg | 1344 |
| Ala | Leu | Asp | Pro | Val | Gln | Asn | Val | Ala | Arg | Arg | Lys | Gly | Arg | Gly | Met |
| | | 435 | | | | | 440 | | | | | 445 | | | |

| ccc | gcg | ccc | gaa | tcc | gtc | agg | gcc | gcc | atc | gcg | gag | gcg | cgt | cag | gaa | 1392 |
| Pro | Ala | Pro | Glu | Ser | Val | Arg | Ala | Ala | Ile | Ala | Glu | Ala | Arg | Gln | Glu |
| | 450 | | | | | 455 | | | | | 460 | | | | |

| ttg | gac | gcc | gac | aag | gcc | tgg | cta | gag | gac | cgg | cgc | gcc | ggg | ctg | gcc | 1440 |
| Leu | Asp | Ala | Asp | Lys | Ala | Trp | Leu | Glu | Asp | Arg | Arg | Ala | Gly | Leu | Ala |
| 465 | | | | | 470 | | | | | 475 | | | | | 480 |

| gat | gcg | gat | gcg | gcg | ctg | gag | gag | gcg | gtg | gcc | ggc | atc | acg | acc | tga | 1488 |
| Asp | Ala | Asp | Ala | Ala | Leu | Glu | Glu | Ala | Val | Ala | Gly | Ile | Thr | Thr | |
| | | | | 485 | | | | | 490 | | | | | 495 | |

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:synthetic
      DNA
<220> FEATURE:
<221> NAME/KEY: modified_base
<222> LOCATION: 6
<223> OTHER INFORMATION: n = inosine
<220> FEATURE:
<221> NAME/KEY: modified_base
<222> LOCATION: 9
<223> OTHER INFORMATION: n = inosine
<220> FEATURE:
<221> NAME/KEY: modified_base
<222> LOCATION: 18
<223> OTHER INFORMATION: n = inosine

<400> SEQUENCE: 3
atgacnccnc ayaayccnga ygc                                          23

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence:synthetic
      DNA
<220> FEATURE:
<221> NAME/KEY: modified_base
<222> LOCATION: 15
<223> OTHER INFORMATION: n = inosine
<220> FEATURE:
<221> NAME/KEY: modified_base
<222> LOCATION: 18
<223> OTHER INFORMATION: n = inosine
<220> FEATURE:
<221> NAME/KEY: modified_base
<222> LOCATION: 24
<223> OTHER INFORMATION: i
<220> FEATURE:
<221> NAME/KEY: modified_base
<222> LOCATION: 27
<223> OTHER INFORMATION: n = inosine

<400> SEQUENCE: 4
ccdatytgca tyttnccngc racnganccd atytc                             35

-continued

```
<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 5
cgccatggcc ccgcataacc cagatgccac c                              31

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 6
aaacaagctt cgtcatggct atcccctc                                  28
```

MODIFIED ETHYLENEDIAMINE-N, N'-DISUCCINATE: ETHYLENEDIAMINE LYASE

CROSS REFERENCE TO PRIOR APPLICATION

This is a U.S. national phase application under 35 U.S.C. §371 of International Application No. PCT/JP2004/007226 filed May 20, 2004. The International Application was published in Japanese on Dec. 1, 2005 as International Publication No. WO 2005/113766 under PCT Article 21(2). All of these prior applications are hereby incorporated by reference in their entireties.

TECHNICAL FIELD

The present invention relates to a novel protein having an ethylenediamine-N,N'-disuccinate:ethylenediamine lyase activity and a gene encoding such protein. Further, the present invention relates to a modified ethylenediamine-N,N'-disuccinate:ethylenediamine lyase that can be derived as a mutant of the enzyme; a gene encoding the modified ethylenediamine-N,N'-disuccinate:ethylenediamine lyase; a recombinant DNA containing a gene DNA encoding the modified ethylenediamine-N,N'-disuccinate:ethylenediamine lyase; a transformant or transductant bearing the recombinant DNA containing the gene encoding the modified ethylenediamine-N,N'-disuccinate:ethylenediamine lyase; and a method for producing diaminoalkylene-N,N'-disuccinates by using such a transformant or transductant.

BACKGROUND ART

Diaminoalkylene-N,N'-disuccinates are important as intermediates of synthesis of medicines and agricultural chemicals, and have a unique property to capture heavy metals. Therefore, optically active forms of such compounds, which may be susceptible to biodegradation once released in nature, are expected to be potentially useful as chelating agents, builders for detergents, etc.

Previously, the present inventors proposed a novel method for efficiently preparing optically active S,S-diaminoalkylene-N,N'-disuccinates from fumaric or maleic acid, and various amines by utilizing the catalytic action of the microorganism [JP Patent Publication (Kokai) Nos. 9-140390A (1997), 9-289895A (1997), and 10-52292A (1998)]. Further, we were successful in increasing a catalytic activity of the microorganism and improving a productivity of the microorganism by isolating and identifying an ethylenediamine-N, N'-disuccinate:ethylenediamine lyase gene followed by genetic recombination [JP Patent Publication (Kokai) No. 10-210984A (1998)].

In general, it is well known that a fumarase is present in microbial cells. Fumarase is an enzyme used to produce malic acid by adding water to fumaric acid. Therefore, when diaminoalkylene-N,N'-disuccinates are prepared by using microorganisms having an ethylenediamine-N,N'-disuccinate:ethylenediamine lyase activity, a fumarase in the microbial cells needs to be inactivated for preventing generation of by-products such as malic acid and the like. In order to do so, the present inventors previously found that when the microbial cells are treated in an alkaline aqueous solution, a fumarase activity in the cells can be reduced [JP Patent Publication (Kokai) No. 11-196882A (1999)].

In the above method for inactivating a fumarase, the inactivation rate of fumarase depends on the treatment temperature. Thus, the higher is the treatment temperature, the faster the inactivation. Moreover, the stability of fumarase varies with host microorganisms, but even when a microorganism whose fumarase is not inactivated readily is used, a higher treatment temperature is preferred. Accordingly, the objective of the present invention is to provide an ethylenediamine-N,N'-disuccinate:ethylenediamine lyase having improved heat resistance.

DESCRIPTION OF THE INVENTION

Vigorous investigation for attaining the above objective by the present inventors has led to the discovery that in the amino acid sequence of ethylenediamine-N,N'-disuccinate:ethylenediamine lyase derived from novel *Brevundimonas diminuta* strain MR-E001, by substituting at least one or more amino acid residues with residues selected from the group of natural amino acids, heat resistance of the enzyme is improved. Thereby, the present invention has been completed. Specifically, the present invention includes:

(1) A protein comprising an amino acid sequence described in SEQ ID NO: 1, and having an ethylenediamine-N,N'-disuccinate:ethylenediamine lyase activity.

(2) A protein comprising an amino acid sequence derived from the amino acid sequence of SEQ ID NO: 1 by deletion, substitution, or addition of one or more amino acid residues, and having an ethylenediamine-N,N'-disuccinate:ethylenediamine lyase activity.

(3) A protein comprising an amino acid sequence derived from the amino acid sequence of SEQ ID NO: 1 by substitution of at least one amino acid residue of a lysine residue at 120, an isoleucine residue at 166, and an alanine residue at 365 with a different amino acid residue, and having an ethylenediamine-N,N'-disuccinate:ethylenediamine lyase activity.

(4) A protein comprising an amino acid sequence derived from the amino acid sequence of SEQ ID NO: 1 by substitution of at least a lysine residue at 120 with glutamic acid, and having an ethylenediamine-N,N'-disuccinate:ethylenediamine lyase activity.

(5) A protein comprising an amino acid sequence derived from the amino acid sequence of SEQ ID NO: 1 by substitution of at least the isoleucine residue at 166 with serine, and having an ethylenediamine-N,N'-disuccinate:ethylenediamine lyase activity.

(6) A protein comprising an amino acid sequence derived from the amino acid sequence of SEQ ID NO: 1 by substitution of at least an isoleucine residue at 166 with threonine, and having an ethylenediamine-N,N'-disuccinate:ethylenediamine lyase activity.

(7) A protein comprising an amino acid sequence derived from the amino acid sequence of SEQ ID NO: 1 by substitution of at least an alanine residue at 365 with valine, and having an ethylenediamine-N,N'-disuccinate:ethylenediamine lyase activity.

(8) A protein comprising an amino acid sequence derived from the amino acid sequence of SEQ ID NO: 1 by substitution of at least a lysine residue at 120 with glutamic acid and an isoleucine residue at 166 with serine, and having an ethylenediamine-N,N'-disuccinate:ethylenediamine lyase activity.

(9) A protein comprising an amino acid sequence derived from the amino acid sequence of SEQ ID NO: 1 by substitution of at least a lysine residue at 120 with glutamic acid and an isoleucine residue at 166 with threonine, and having an ethylenediamine-N,N'-disuccinate:ethylenediamine lyase activity.

(10) A protein comprising an amino acid sequence derived from the amino acid sequence of SEQ ID NO: 1 by substitution of at least an isoleucine residue at 166 with serine and an alanine residue at 365 with valine, and having an ethylenediamine-N,N'-disuccinate:ethylenediamine lyase activity.

(11) A protein comprising an amino acid sequence derived from the amino acid sequence of SEQ ID NO: 1 by substitution of at least an isoleucine residue at 166 with threonine and an alanine residue at 365 with valine, and having an ethylenediamine-N,N'-disuccinate:ethylenediamine lyase activity.

(12) A protein comprising an amino acid sequence derived from the amino acid sequence of SEQ ID NO: 1 by substitution of at least a lysine residue at 120 with glutamic acid and an isoleucine residue at 166 with serine an alanine residue at 365 with valine, and having an ethylenediamine-N,N'-disuccinate:ethylenediamine lyase activity.

(13) A protein comprising an amino acid sequence derived from the amino acid sequence of SEQ ID NO: 1 by substitution of at least a lysine residue at 120 with glutamic acid and an isoleucine residue at 166 with threonine and an alanine residue at 365 with valine, and having an ethylenediamine-N,N'-disuccinate:ethylenediamine lyase activity.

(14) A gene encoding the protein according to (1).

(15) A gene of the following (a) or (b):

(a) a gene comprising a nucleotide sequence described in SEQ ID NO: 2; or (b) a gene that hybridizes under stringent conditions to a DNA comprising a sequence complementary to a DNA comprising the nucleotide sequence of SEQ ID NO: 2 or a portion thereof, and encodes a protein having an ethylenediamine-N,N'-disuccinate:ethylenediamine lyase activity.

(16) A gene encoding the protein according to (2).

(17) The gene according to (16) comprising a nucleotide sequence derived from the nucleotide sequence of SEQ ID NO: 2 by deletion, substitution or addition of one or more bases.

(18) A gene encoding the protein according to (3).

(19) The gene according to (18) comprising a nucleotide sequence derived from the nucleotide sequence of SEQ ID NO: 2 by substitution of at least one base of bases from 358 to 360, from 496 to 498, and from 1093 to 1095 with a different base.

(20) A gene encoding the protein according to (4).

(21) The gene according to (20) comprising a nucleotide sequence derived from the nucleotide sequence of SEQ ID NO: 2 by substitution of bases AAA from 358 to 360 with GAA or GAG.

(22) The gene according to (20) comprising a nucleotide sequence derived from the nucleotide sequence of SEQ ID NO: 2 by substitution of a base, adenine, at 358 with guanine.

(23) A gene encoding the protein according to (5).

(24) The gene according to (23) comprising a nucleotide sequence derived from the nucleotide sequence of SEQ ID NO: 2 by substitution of bases ATC from 496 to 498 with AGC, AGT, or TCN (N refers to A, G, C or T).

(25) The gene according to (23) comprising a nucleotide sequence derived from the nucleotide sequence of SEQ ID NO: 2 by substitution of the base, thymine, at 497 with guanine.

(26) A gene encoding the protein according to (6).

(27) The gene according to (26) comprising a nucleotide sequence derived from the nucleotide sequence of SEQ ID NO: 2 by substitution of bases ATC from 496 to 498 with ACN (N refers to A, G, C or T).

(28) The gene according to (26) comprising a nucleotide sequence derived from the nucleotide sequence of SEQ ID NO: 2 by substitution of a base, thymine, at 497 with cytosine.

(29) A gene encoding the protein according to (7).

(30) The gene according to (29) comprising a nucleotide sequence derived from the nucleotide sequence of SEQ ID NO: 2 by substitution of bases GCC from 1093 to 1095 with GTN (N refers to A, G, C or T).

(31) The gene according to (29) comprising a nucleotide sequence derived from the nucleotide sequence of SEQ ID NO: 2 by substitution of a base, cytosine, at 1094 with thymine.

(32) A gene encoding the protein according to (8).

(33) The gene according to (32) comprising a nucleotide sequence derived from the nucleotide sequence of SEQ ID NO: 2 by substitution of bases AAA from 358 to 360 with GAA or GAG, and bases ATC from 496 to 498 with AGC, AGT, or TCN (N refers to A, G, C or T).

(34) The gene according to (32) comprising a nucleotide sequence derived from the nucleotide sequence of SEQ ID NO: 2 by substitution of a base, adenine, at 358 with guanine, and a base, thymine, at 497 with guanine.

(35) A gene encoding the protein according to (9).

(36) The gene according to (35) comprising a nucleotide sequence derived from the nucleotide sequence of SEQ ID NO: 2 by substitution of bases AAA from 358 to 360 with GAA or GAG, and bases ATC from 496 to 498 with ACN (N refers to A, G, C or T), respectively.

(37) The gene according to (35) comprising a nucleotide sequence derived from the nucleotide sequence of SEQ ID NO: 2 by substitution of a base, adenine, at 358 with guanine, and a base, thymine, at 497 with cytosine, respectively.

(38) A gene encoding the protein according to (10).

(39) The gene according to (38) comprising a nucleotide sequence derived from the nucleotide sequence of SEQ ID NO: 2 by substitution of bases ATC from 496 to 498 with AGC, AGT, or TCN (N refers to A, G, C or T), and bases GCC from 1093 to 1095 with GTN (N refers to A, G, C or T), respectively.

(40) The gene according to (38) comprising a nucleotide sequence derived from the nucleotide sequence of SEQ ID NO: 2 by substitution of a base, thymine, at 497 with guanine, and a base, cytosine, at 1094 with thymine, respectively.

(41) A gene encoding the protein according to (11).

(42) The gene according to (41) comprising a nucleotide sequence derived from the nucleotide sequence of SEQ ID NO: 2 by substitution of bases ATC from 496 to 498 with ACN (N refers to A, G, C or T), and bases GCC from 1093 to 1095 with GTN (N refers to A, G, C or T), respectively.

(43) The gene according to (41) comprising a nucleotide sequence derived from the nucleotide sequence of SEQ ID NO: 2 by substitution of a base, thymine, at 497 with cytosine, and a base, cytosine, at 1094 with thymine, respectively.

(44) A gene encoding the protein according to (12).

(45) The gene according to (44) comprising a nucleotide sequence derived from the nucleotide sequence of SEQ ID NO: 2 by substitution of bases AAA from 358 to 360 with GAA or GAG, bases ATC from 496 to 498 with AGC, AGT, or TCN (N refers to A, G, C or T), and bases GCC from 1093 to 1095 with GTN (N refers to A, G, C or T), respectively.

(46) The gene according to (44) comprising a nucleotide sequence wherein the base, adenine, at 358 is substituted with guanine, the base, thymine, at 497 with guanine, and the base, cytosine, at 1094 with thymine in the nucleotide sequence of SEQ ID NO: 2.

(47) A gene encoding the protein according to (13).

(48) The gene according to (47) comprising a nucleotide sequence derived from the nucleotide sequence of SEQ ID NO: 2 by substitution of bases AAA from 358 to 360 with GAA or GAG, bases ATC from 496 to 498 with ACN (N refers to A, G, C or T), and bases GCC from 1093 to 1095 with GTN (N refers to A, G, C or T), respectively.

49) The gene according to (47) comprising a nucleotide sequence derived from the nucleotide sequence of SEQ ID NO: 2 by substitution of a base, adenine, at 358 with guanine, a base, thymine, at 497 with cytosine, and a base, cytosine, at 1094 with thymine, respectively.

(50) A recombinant wherein the gene DNA according to any one of (14) to (49) is inserted into a DNA vector.

(51) A transformant or transductant comprising the recombinant DNA according to (50).

(52) A method of producing an ethylenediamine-N,N'-disuccinate:ethylenediamine lyase, comprising a step of culturing the transformant or transductant according to (51) to collect the ethylenediamine-N,N'-disuccinate:ethylenediamine lyase from the resulting culture.

(53) A method of producing a diaminoalkylene-N,N'-disuccinate, comprising a step of reacting fumaric acid and a diamine in the presence of the transformant or transductant according to (51) to collect the diaminoalkylene-N,N'-disuccinate from the resulting reaction products.

Figure 1:
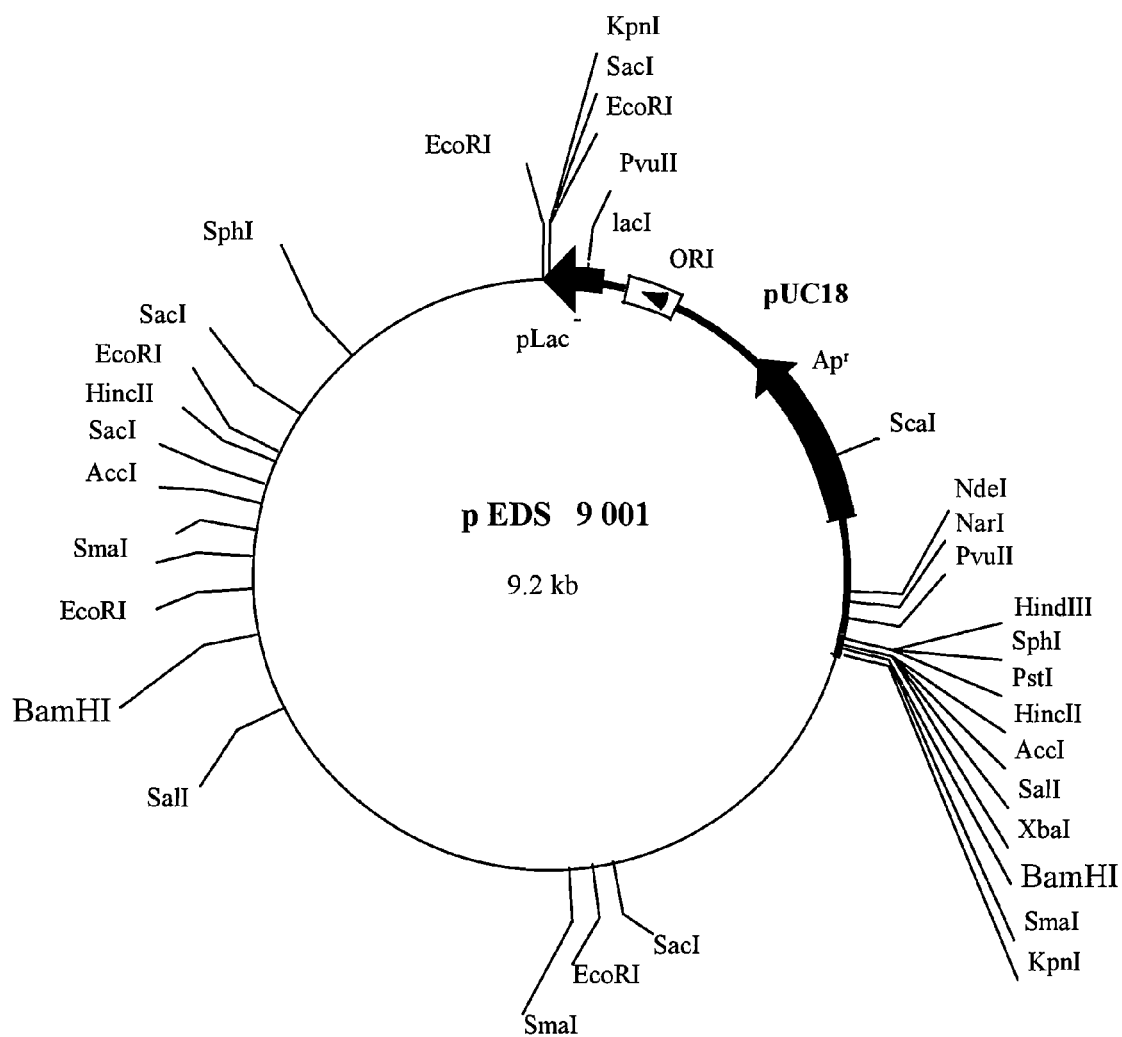
FIG. 1 is a restriction map of the plasmid pEDS9001.

The present invention is described in detail below. In the present invention, the ethylenediamine-N,N'-disuccinate: ethylenediamine lyase (also named "EDDSase") refers to an enzyme capable of reversibly producing ethylenediamine-N,N'-disuccinate from fumaric acid and ethylenediamine, but it may produce ethylenediamine-N-monosuccinic acid depending on reaction conditions. Further, the present enzyme also reacts on other diamines in addition to ethylenediamine, producing corresponding diaminoalkylene-N,N'-disuccinates. Further, many of resulting diaminoalkylene-N,N'-disuccinates are optically active forms, but some generated by the enzyme are racemic compounds. A group of enzymes exhibiting such reactivity have been found in bacteria belonging to plural genera that have been isolated and identified from nature by the present inventors. These bacteria are described in the above JP Patent Publication (Kokai) Nos. 9-140390A (1997), 9-289895A (1997), and 10-52292A (1998). Moreover, the present applicants were successful not only in isolating from *Brevundimonas* sp. strain TN-3 described in Patent Publication (Kokai) No. 10-52292A (1998) an ethylenediamine-N,N'-disuccinate:ethylenediamine lyase gene to spell out the amino acid sequence and the gene sequence thereof for the first time, but also in forming transformants that potentially can express the gene product thereof in large quantities [JP Patent Publication (Kokai) No. 10-210984A (1998)].

On the other hand, recent advancement in recombinant DNA technology makes it possible to form variants wherein one or more amino acids that constitute an enzyme are lost, added, deleted, inserted, or substituted with other amino acids, without essentially changing the action of such an enzyme. It is known that compared with the wild type enzyme without mutation, depending on the locations of amino acid residues substituted, lost, added, deleted, or inserted as well as types of amino acids substituted, these variants may exhibit significantly improved properties such as resistance to organic solvents, heat resistance, acid resistance, alkali resistance, substrate specificity, and substrate affinity. These improved properties may result in more stable enzymes as catalysts, simpler reaction processes, increased reaction yields, etc., and thereby may contribute to great reduction in production cost in manufacturing where enzyme reactions are utilized. Therefore, attempts are made to improve various properties in a large number of enzymes to develop useful modified enzymes.

Herein, "wild type" means that an amino acid sequence that constitutes an enzyme kept in a microorganism separated from nature, and a nucleotide sequence encoding such an enzyme are, either intentionally or unintentionally, not lost, deleted, inserted, or substituted with other amino acids or bases.

The present inventors conducted screening of microorganisms having such an enzyme activity for further useful ethylenediamine-N,N'-disuccinate:ethylenediamine lyase. As a result, *Brevundimonas diminuta* strain MR-E001 (hereinafter also referred to the MR-E001 strain), which has a high activity of the enzyme, was isolated, and an ethylenediamine-N,N'-disuccinate:ethylenediamine lyase gene was obtained from the MR-E001 strain. In addition, it was discovered that in the amino acid sequence of the enzyme, by substituting at least one or more amino acid residues with residues selected from the group of natural amino acids, heat resistance of the enzyme is improved. Thereby, the present invention has been completed.

The modified ethylenediamine-N,N'-disuccinate:ethylenediamine lyase of the present invention can be obtained, for example, by the following method. First, from the MR-E001 strain, a wild type ethylenediamine-N,N'-disuccinate:ethylenediamine lyase gene is obtained. For obtaining the gene, any known technique can be used. For example, chromosomal DNA prepared from the MR-E001 strain is used as a template and PCR (Polymerase Chain Reaction) is conducted to obtain a DNA fragment containing a part of the gene. For the primers used for PCR, in general, degenerate primers can be used, which are designed based on the amino acid sequence obtained by amino acid analysis after isolation and purification of the enzyme. Further, when the sequence of the gene of interest is expected to be homologous with a sequence of the gene derived from a different species that has been already known, or when a gene homologous with a sequence of the gene derived from a different species that has been already known is to be obtained, degenerate primers can be designed for PCR according to the amino acid sequence information encoded by such a known gene derived from the different species. By using the primers designed thereby, the chromosomal DNA from the MR-E001 strain is used as a template and PCR is conducted, and the resulting amplified DNA product is used as a probe for colony hybridization that will be conducted later.

Next, a DNA library is prepared. The chromosome from the MR-E001 strain prepared according to a known method, for example, the method made by Saito and Miura [Biochem. Biophys. Acta, 72, 619 (1963)], is cleaved or partially cleaved by a suitable restriction enzyme, which is then ligated to a vector DNA that has been treated by a restriction enzyme that can generate cleaved terminals linkable to such cleaved terminals of the restriction enzyme described above, so that transformants or transductants of a suitable microorganism host are formed, and thereby the DNA library of the chromosome is produced. Examples of the microorganisms that can be hosts for the transformants or the transductants include, when *Escherichia coli* is used, *E. coli* strain K12, strain JM109, strain XL1-Blue, etc., but should not be particularly limited to these. Examples of the plasmid DNA used for forming the transformants include, when *E. coli* is the host, pBR322, pUC18, pBluescript II SK(+), etc., which have auto-replicable regions in *E. coli*. Further, the vector DNA should not be limited to the above plasmid vector DNAs, but phage vector DNAs may be used to form transductants.

Herein, in describing gene manipulation processes, microorganisms containing a recombinant DNA of interest are referred to as transformants when plasmid vector DNAs are used, and transductants when phage vector DNAs are used. All of the above transformants and transductants are included in the present invention. Examples, wherein transformants are created utilizing plasmid vector DNAs, are described below.

Colony hybridization is conducted for the resulting DNA library of the chromosome, using the PCR-amplified DNA product described above as a probe. The colony hybridization may be an ordinary method. For example, the one described below can be used. Specifically, transformants from the chromosomal DNA library grown on an agar medium are transferred to a nylon membrane, and then the DNA is fixed by cytolysis. The amplified DNA product by PCR described above is rendered to be a probe by labeling, for example, using a DNA Labeling kit (from Roche Diagnostics), and then hybridized with the membrane. Positive clones can be selected, for example, by using a DNA Luminescent Detection kit (from Roche Diagnostics). From the resulting positive clones, plasmid DNA is prepared according to the ordinary method, optionally subcloning is conducted, and then nucleotide sequences of the inserted fragments are determined. Any method can be used for the determination of the nucleotide sequences, and usually the nucleotide sequences can be determined by the dideoxy method (Methods in Enzymology, 101, 20-78, 1983) using a commercial kit or the like. Thus, the wild type ethylenediamine-N,N'-disuccinate:ethylenediamine lyase gene derived from the MR-E001 strain can be obtained, and also an amino acid sequence and a nucleotide sequence thereof can be determined.

Next, for obtaining a modified ethylenediamine-N,N'-disuccinate:ethylenediamine lyase, wherein in the amino acid sequence of the resulting wild type ethylenediamine-N,N'-disuccinate:ethylenediamine lyase, at least one amino acid residue is substituted with a different natural amino acid residue, any method can be used and usually a well known method can be used. Specifically, examples of methods for treating the wild type ethylenediamine-N,N'-disuccinate:ethylenediamine lyase gene DNA include: to contact and react a mutagenic chemical such as hydroxylamine and nitrous acid; to induce mutations by irradiating ultraviolet rays; to induce mutations on a random basis by using PCR; to generate site-specific substitutions by utilizing a commercial kit; to selectively cleave gene DNA and then remove and add selected oligonucleotides for ligation; and the like.

After an ethylenediamine-N,N'-disuccinate:ethylenediamine lyase gene DNA having a distinct mutation caused by any one of the above treatments is produced, transformants is formed. As the plasmid vectors that can be used for transformation, for example, when *E. coli* is the host, those plasmid vectors included in the step for preparing the DNA library described above may be used, but it is preferable to use an expression vector with high expression efficiency, such as an expression vector, pKK233-2 (from Amersham), which has a trc promoter, or a derivative of pKK233-2, i.e., pFY529V, which will be described later in an example, in order to efficiently detect a remaining activity of ethylenediamine-N, N'-disuccinate:ethylenediamine lyase after heat treatment in the later step for screening.

However, the vectors and the hosts used in the present invention should not be limited to those plasmids described above and *E. coli*. Examples of the vectors include plasmid DNA, bacteriophage DNA, retrotransposon DNA, artificial chromosomal DNA, etc.

The ethylenediamine-N,N'-disuccinate:ethylenediamine lyase gene DNA of the present invention requires genes to be incorporated into a vector, so that the gene DNA can be expressed in a host thereof. Therefore, to the vector of the present invention, in addition to the gene DNA of the present invention, a promoter, a terminator, an enhancer, a splicing signal, a poly-A addition signal, a selection marker, a ribosome-binding sequence (SD sequence), etc., can be linked. Further, examples of the selection markers include a dihydrofolate reductase gene, an ampicillin resistance gene, a neomycin resistance gene, etc.

The transformant of the present invention can be obtained by transferring the recombinant vector of the present invention into a host in a manner that the ethylenediamine-N,N'-disuccinate:ethylenediamine lyase gene can be expressed. Examples of the hosts include bacteria such as *E. coli, Bacillus subtilis*, etc. In addition, yeast, animal cells, insect cells, plant cells, etc., can be also used.

Examples of bacteria from the genus of *Escherichia* include *Escherichia coli*, etc., and examples of bacteria from the genus of *Bacillus* include *Bacillus subtilis*, etc. There should be no particular restriction on how recombinant vectors are transferred into bacteria, and any technique for transferring DNA into bacteria can be used. Examples of such techniques include: to utilize calcium ions; electroporation; and the like.

When yeast is the host, for example, *Saccharomyces cerevisiae, Schizosaccharomyces pombe, Pichia pastoris*, etc., are used. There should be no particular restriction on how recombinant vectors are transferred into yeast, and any technique for transferring DNA into yeast can be used. Examples of such techniques include: electroporation; the spheroplast method; the lithium acetate method; and the like.

When animal cells are the host, monkey COS-7 cells, Vero cells, CHO cells; mouse L cells; rat GH3 cells; human FL cells; and the like are used. Examples of techniques for transferring recombinant vectors into animal cells include: electroporation; the Ca-phosphate method; lipofection; and the like.

When insect cells are the host, Sf9 cells, Sf21 cells, and the like are used. Examples of techniques for transferring recombinant vectors into insect cells include: the Ca-phosphate method; lipofection; electroporation; and the like.

When plant cells are the host, examples include corn, rice, tobacco, and the like, but should not be limited to these. Examples of technique for transferring recombinant vectors into plant cells include: the Agrobacterium method; the particle gun method; the PEG method; electroporation; and the like.

As described above, various transformants that bear recombinant DNA containing the ethylenediamine-N,N'-disuccinate:ethylenediamine lyase gene can be provided.

When a host is *E. coli*, the resulting transformants are cultured on an agar medium to form colonies followed by liquid culture to produce an ethylenediamine-N,N'-disuccinate:ethylenediamine lyase. The resulting culture, for example, is subjected to heat treatment for 30 min. at 40 to 65° C. followed by the determination of remaining ethylenediamine-N,N'-disuccinate:ethylenediamine lyase activities. A transformant with a higher remaining ethylenediamine-N,N'-disuccinate:ethylenediamine lyase activity is selected. A nucleotide sequence of the ethylenediamine-N,N'-disuccinate:ethylenediamine lyase gene inserted into the recombinant DNA of the resulting superior transformant thereby can be determined, for example, by the dideoxy method.

The nucleotide sequence of the ethylenediamine-N,N'-disuccinate:ethylenediamine lyase gene DNA of the present invention is represented by SEQ ID NO: 2, and an amino acid sequence encoded by the gene of the present invention is represented by SEQ ID NO: 1.

Further, it may be possible to develop a mutated enzyme whose heat resistance is more improved than a single mutant by combining plural different single-substitution mutations, each of which provides heat resistance to the enzyme, to form a multiple mutant. Any technique can be used for forming a multiple mutant, and examples include: to generate a site-specific substitution by using an artificial single-strand oligo-nucleotide; to cleave a DNA fragment containing multiple different single mutated sites by restriction enzymes, which are then ligated; and the like.

Therefore, as long as the ethylenediamine-N,N'-disuccinate:ethylenediamine lyase has its activity, mutation by deletion, substitution, addition, and the like can arise at a plurality of, preferably one or some, amino acids in the amino acid sequence of SEQ ID NO: 1. For example, from 1 to 10, preferably from 1 to 5, amino acids may be deleted from the amino acid sequence of SEQ ID NO: 1; from 1 to 10, preferably from 1 to 5, amino acids may be added to the amino acid sequence of SEQ ID NO: 1; or from 1 to 10, preferably from 1 to 5, amino acids in the amino acid sequence of SEQ ID NO: 1 may be substituted with other amino acids.

Particularly, in the present invention, it is preferable that at least one amino acid of Lys at 120, Ile at 166, and Ala at 365 is substituted by a different amino acid in the amino acid sequence of SEQ ID NO: 1. The amino acid substitutions at the above three locations can be optionally combined. Aspects of preferred substitutions are shown below, wherein in the following aspects of substitutions, numerals refer to location numbers in the amino acid sequence of SEQ ID NO: 1; letters in the left side of the numbers refer to amino acids (in single letters) before substitution; and letters in the right side of the numbers refer to amino acids (in single letters) after substitution.

K120E

I166S

I166T

A365V (K120E, I166S)

(K120E, I166T)

(I166S, A365V)

(I166T, A365V)

(K120E, I166S, A365V)

(K120E, I166T, A365V)

Moreover, a base substitution so as to generate the substitution of K120E is described below.

The locations in the nucleotide sequence of SEQ ID NO: 2 corresponding to Lys at 120 are from 358 to 360, and the nucleotide sequence is "AAA." On the other hand, the codon for glutamic acid is GAA or GAG. Hence, in the present invention, bases can be substituted so that AAA becomes GAA or GAG. In particular, it is preferable that A at 358 is substituted with G (AAA→GAA).

Similarly to the above, so as to generate the substitution of I166S, in the nucleotide sequence of SEQ ID NO: 2, the bases ATC from 496 to 498 can be substituted with AGC, AGT, ACA, ACC, ACG, or ACT. In particular, it is preferable that T at 497 is substituted with G (ATC→AGC). So as to generate the substitution of I166T, in the nucleotide sequence of SEQ ID NO: 2, the bases ATC from 496 to 498 can be substituted with ACA, ACC, ACG, or ACT. In particular, it is preferable that T at 497 is substituted with C (ATC→ACC).

So as to generate the substitution of A365V, in the nucleotide sequence of SEQ ID NO: 2, the bases GCC from 1093 to 1095 can be substituted with GTA, GTG, GTC, or GTT. In particular, it is preferable that C at 1094 is substituted with T (GCC→GTC).

However, in the present invention, the amino acids after substitution should not be limited to the above examples. Thus, so as that at least one amino acid residue at 120, 166, or 365 in the amino acid sequence of SEQ ID NO: 1 is substituted with a different amino acid from the examples above, at least one base of the codons encoding such amino acids can be substituted with another base.

Herein, "ethylenediamine-N,N'-disuccinate:ethylenediamine lyase activity" refers to a catalytic activity to produce a diaminoalkylene-N,N'-disuccinate by reacting fumaric acid and a diamine.

Furthermore, a gene that hybridizes under stringent conditions to DNA made of a sequence complementary to the DNA made of the nucleotide sequence of SEQ ID NO: 2 or a part of such a sequence, and also encodes a protein having the ethylenediamine-N,N'-disuccinate:ethylenediamine lyase activity is included in the gene of the present invention. The stringent conditions refer to typical conditions in which specific hybridization occurs. Examples include conditions where highly homologous nucleic acids, i.e., DNAs with 80% or more, preferably 90% or more, homology, also each DNA encoding a protein having the ethylenediamine-N,N'-disuccinate:ethylenediamine lyase activity, hybridize each other, whereas DNAs with less homology do no hybridize each other. More specifically, it refers to conditions in which the sodium concentration is from 300 to 2000 mM, preferably from 600 to 900 mM, and the temperature is from 40 to 75° C., preferably from 55 to 65° C.

Once the nucleotide sequence of the present invention is determined, the gene DNA of the present invention can be thereafter obtained by PCR, wherein chemically synthesized or cloned DNA is a template, or by hybridization using a DNA fragment having such a nucleotide sequence as a probe.

In the present invention, the heat resistance refers to a property capable of retaining the enzyme activity even in the temperature range where the wild type ethylenediamine-N,N'-disuccinate:ethylenediamine lyase is deactivated. Such a temperature range is from 45 to 60° C., preferably from 50 to 60° C. In the range of from 50 to 60° C., modified ethylenediamine-N,N'-disuccinate:ethylenediamine lyase can retain 60% of the enzyme activity exhibited at 50° C.

The resulting transformant bearing the recombinant plasmid DNA containing the modified ethylenediamine-N,N'-disuccinate:ethylenediamine lyase gene wherein a single mutation or multiple mutations are transferred can be used to produce an ethylenediamine-N,N'-disuccinate:ethylenediamine lyase. In addition, the above transformant (e.g., an *E. coli* transformant) can be used to produce diaminoalkylene-N,N'-succinic acids.

For producing the ethylenediamine-N,N'-disuccinate:ethylenediamine lyase, the above transformant can be cultured to collect the ethylenediamine-N,N'-disuccinate:ethylenediamine lyase from such a culture. The term "culture" refers to any of culture supernatant, cultured cells or cultured cell mass; or destructed cells or cell mass. For culturing the transformant of the present invention, an ordinary method used for culturing a host is followed.

For a medium for culturing a transformant obtained from a bacterial host such as *E. coli* or yeast, any medium, natural or synthetic, containing a carbon source, a nitrogen source, inorganic salts, etc., that can be utilized by the microorganism and capable of efficiently culturing the transformant can be used. Examples of carbon sources include carbohydrates such as glucose, fructose, sucrose, starch; organic acids such as acetic acid, propionic acid; and alcohols such as ethanol, propanol. Examples of nitrogen sources include ammonia; ammonium salts of inorganic and organic acids such as ammonium chloride, ammonium sulfate, ammonium acetate, and ammonium phosphate, and other nitrogen-containing compounds, as well as peptone, meat extract, corn steep liquor, and the like. Examples of inorganic salts include potassium dihydrogenphosphate, potassium hydrogenphosphate, magnesium phosphate, magnesium sulfate, sodium chloride, ferrous sulfate, manganese sulfate, copper sulfate, calcium carbonate. The culture is usually performed under aerobic conditions such as shake culture, or culture by aeration with stirring. With a solution containing an inorganic or organic acid, or an alkali, the pH is adjusted. During the culture, an antibiotic such as ampicillin or tetracycline may be optionally added to the medium.

When a microorganism transformed with an expression vector using a promoter is cultured and the promoter is inductive, an inducer may be optionally added to the medium. For example, when a microorganism transformed with an expression vector having a promoter that is inducible with isopropyl-β-D-thiogalactoside (IPTG) is cultured, IPTG, etc., can be added to the medium. Further, when a microorganism transformed with an expression vector using a trp promoter that is inducible with indoleacetic acid (IAA) is cultured, IAA, etc., can be added to the medium.

Examples of media for culturing a transformant obtained from an animal cell host include media such as general ones, e.g., a RPMI1640 medium and a DMEM medium; or a medium wherein fetal bovine serum, etc., are added to a RPMI1640 or DMEM medium. The culture is usually performed under 5% $CO_2$ at 37° C. for from 1 to 30 days. During the culture, an antibiotic such as kanamycin or penicillin may be optionally added to the medium.

When the protein of the present invention is produced within the cell mass or cells following the culture, the protein of interest is collected by destructing the cell mass or the cells by ultrasonic, repeated freeze and thawing, homogenizing, etc. Further, when the protein of the present invention is produced outside a microorganism or cells, the culture solution per se is used, or the microorganism or the cells are removed by centrifugation or the like. Then, the protein of the present invention can be isolated and purified by an ordinary biochemical technique used for protein isolation and purification. Examples of such techniques include ammonium sulfate precipitation, gel chromatography, ion-exchange chromatography, and affinity chromatography, which may be used alone or in any proper combination thereof.

When a transformant is a plant cell or plant tissue, the culture can be performed by using an ordinary plant culture medium, for example, an MS basal medium, LS basal medium, etc. Any ordinary culture method, either liquid culture or solid culture, can be used.

For purifying the protein of the present invention from the culture, cells are first destructed by cytolysis using an enzyme such as cellulase and pectinase, ultrasonic destruction, grinding, and the like. Then, insoluble matters are removed by filtration or centrifugation to obtain a crude protein solution. The protein of the present invention is purified from the above crude solution by salt precipitation, chromatography of various types (e.g., gel filtration chromatography, ion-exchange chromatography, affinity chromatography, etc.), SDS-polyacrylamide gel electrophoresis, and the like, or optionally the combination thereof.

The production of the diaminoalkylene-N,N'-disuccinate is described below. An ordinary solid culture may be used for culturing an *E. coli* transformant, but it is preferable to use liquid culture as much as possible. A medium for the culture, for example, containing one or more nitrogen sources such as yeast extract, tryptone, polypeptone, corn steep liquor, percolate of soy bean and wheat bran loaded with one or more inorganic salts such as sodium chloride, potassium dihydrogenphosphate, potassium hydrogenphosphate, magnesium sulfate, magnesium chloride, ferric chloride, ferric sulfate, and manganese sulfate, and optionally further with sugar materials, vitamins, etc., is used. In addition, the initial pH of the medium is suitably adjusted from 7 to 9. Preferably, submerged culture, shake culture, stationery culture, or the like is performed from 25 to 42° C. for from 6 to 24 hrs.

After the completion of the culture, the resulting microbial cells are harvested, washed with a suitable buffer solution, for example, a 50 mM boric acid buffer solution (pH 9.0), and then suspended in the buffer solution to prepare a cell suspension. For example, by heating this cell suspension from 40 to 65° C. for from 30 min. to 72 hrs., a fumarase activity is lost, and microbial mass having the ethylenediamine-N,N'-disuccinate:ethylenediamine lyase activity can be prepared. By suspending the resulting microbial mass in aqueous solutions containing fumaric or maleic acid and various amines to allow them to react, aqueous solutions of optically active S,S-diaminoalkylene-N,N'-disuccinates that do not contain by-products such as malic acid can be prepared.

Moreover, bacteriological properties of *Brevundimonas diminuta* strain MR-E001 are shown in the table below.

TABLE 1

Bacteriological properties of MR-E001 strain

| | |
|---|---|
| Morphology | rod-shaped |
| Gram stain | − |
| Spores | − |
| Mobility | + |
| Flagella | polar flagellation |
| Oxygen requirement | aerobic |
| Oxidase | + |
| Catalase | + |
| OF test | − |
| Color tone of colonies | No characteristic pigment is generated. |
| Production of fluorescent pigment | − |
| Accumulation of PHB | + |
| Auxotrophy | present |
| Quinone system | Q-10 |
| Reduction of nitrates | + |
| Production of Indole | − |
| Arginine dihydrolase | − |
| Urea degradation | − |
| Esculin degradation | − |
| Gelatin liquefaction | − |
| PNPG | − |
| Assimilation | |
| Glucose | − |
| L-Arabinose | − |
| D-Mannose | − |
| D-Mannitol | − |
| N-Acetyl-D-glucosamine | − |
| Maltose | − |
| Potassium gluconate | + |
| n-Capric acid | − |
| Adipic acid | + |
| dl-Malic acid | + |
| Citric acid | + |
| Phenyl acetate | − |

Moreover, *Brevundimonas diminuta* strain MR-E001 was deposited on Feb. 5, 2003, with International Patent Organism Depositary, National Institute of Advanced Industrial Science and Technology (Tsukuba Central 6, 1-1-1 Higashi, Tsukuba, Ibaraki, Japan), under the Accession No. FERM BP-08677.

The present invention is described more in detail by referring to the Examples below. However, the Examples should be considered as being presented for further understanding of the present invention, and do not limit the scope of the present invention by any means.

EXAMPLE 1

Preparation of Wild Type Ethylenediamine-N,N'-Disuccinate:Ethylenediamine Lyase Gene Derived from MR-E001 Strain (1) Preparation of Chromosomal DNA from MR-E001 Strain The MR-E001 strain was cultured with shaking in 100 ml of an EDDS medium [0.2% ethylenediamine-N,N'-disuccinate, 0.2% glucose, 0.1% Bacto yeast extract, 0.05% polypeptone, 0.1% $MgSO_4.7H_2O$, 25% (v/v) phosphate buffer (1M, pH 7.0), a 0.5% (v/v) mixture solution of metal salts (containing 56 g of $NaSO_4$, 8 g of $MgCl_2.6H_2O$, 0.8 g of $CaCl_2$, 0.6 g of $MnSO_4.4H_2O$, 0.12 g of $FeCl_3.6H_2O$, and 0.06 g of $ZnSO_4$ per 100 ml)] at 30° C. for 4 days. Then, the cells were harvested and suspended in 4 ml of a saline-EDTA solution (0.1 M EDTA, 15 M NaCl, pH 8.0), to which 8 mg of lysozyme was added. The resulting suspension was shaken at 37° C. for 1 hr. and then frozen. Next, 10 ml of a Tris-SDS solution (1% SDS, 0.1 M NaCl, 0.1 M Tris, pH 9.0) was gently added thereto while shaking, and further proteinase K (from Merck) was added (at the final concentration of 1 mg) and shaken at 37° C. for 1 hr. Then, an equal volume of TE-saturated phenol (TE:10 mM Tris, 1 mM EDTA, pH 8.0) was added thereto and stirred followed by centrifugation. The upper layer was collected, to which a two-fold volume of ethanol was added, and then DNA was collected by rolling with a glass rod followed by removal of phenol using 90%, 80%, and 70% ethanol in this order. Subsequently, the DNA was dissolved in 3 ml of a TE buffer, to which a ribonuclease A solution (that has been treated by heat at 100° C. for 15 min.) was added at the final concentration of 10 mg/ml to shake at 37° C. for 30 min. Proteinase K was further added to shake at 37° C. for 30 min. Then, an equal volume of TE-saturated phenol was added thereto, which was separated by centrifugation into upper and lower layers to collect the upper layer (hereinafter, this procedure is referred to as phenol extraction). After phenol extraction was repeated twice, an equal volume of chloroform (containing 4% isoamyl alcohol) was added to repeat the similar extraction procedure twice (hereinafter, this procedure is referred to as chloroform extraction). Next, ethanol twice in volume thereof was added to the upper layer, and the DNA was recovered by rolling with a glass rod to obtain a chromosomal DNA sample.

(2) Preparation of Probe

The present applicants previously succeeded in isolating an ethylenediamine-N,N'-disuccinate:ethylenediamine lyase gene from *Brevundimonas* sp. strain TN-3, and determined for the first time the amino acid sequence and the gene sequence thereof [JP Patent Publication (Kokai) No. 10-210984A (1998)]. The degenerate primers used in the above publication, i.e., artificial DNAs having the sequences represented by SEQ ID NO: 3 and SEQ ID NO: 4 (Primer #1 and Primer #2, respectively) were used, and PCR was conducted by using the chromosomal DNA from the MR-E001 strain obtained in step (1).

```
                                            (SEQ ID NO: 3)
Primer #1: ATGACICCIC AYAAYCCIGA YGC (SEQ ID NO: 4)
Primer #2: CCDATYTGCAT YTTICCIGC RACIGAICCD ATYTC
```

Specifically, 1 µl of the chromosomal DNA from the MR-E001 strain, 10 µl of 10× buffer for the reaction, 4 µl of 10 mM dNTP, 1 µl of Primer #1 and 1 µl of Primer #2 (equivalent to 100 pmol, respectively), and 1 µl of ExTaq (from Takara Shuzo) were admixed to obtain a 100 µl solution. The resulting solution was incubated at 95° C. for 30 sec. (denaturation), at 55° C. for 30 sec. (annealing), and at 72° C. for 2 min. (extension) for 30 cycles. After the completion of the reaction, phenol extraction and chloroform extraction were performed to recover the amplified DNA by ethanol precipitation. The resulting DNA was separated by 1.0% agarose gel electrophoresis, and then obtained was a DNA fragment having about 300 bp, which was expected to encode a part of the ethylenediamine-N,N'-disuccinate:ethylenediamine lyase gene of the MR-E001 strain. This DNA fragment obtained thereby was labeled by using a DIG DNA Labeling kit (from Roche Diagnostics) to provide a probe.

(3) Preparation of DNA Library

To 10 μl of the chromosomal DNA from the MR-E001 strain, 5 μl of 10× buffer for restriction digestion, 33 μl of sterile water, and 2 μl of a restriction enzyme KpnI were added to react at 37° C. for 16 hrs., and then the DNA was recovered by ethanol precipitation. DNA fragments from 6.5 Kb to 5.5 Kb were extracted by agarose gel electrophoresis from the gel, which were recovered by using a DNA PREP (from Diatron). These DNA fragments were inserted at the KpnI site of an *E. coli* vector pUC18 by using a DNA Ligation Kit Ver. 1 (from Takara Shuzo) to prepare a recombinant DNA library. The pUC18 fragment used for the ligation was prepared by the process described below. To 2 μl of a solution preserving pUC18, 5 μl of 10× buffer for restriction enzyme, 40 μl of sterile water, and 3 μl of a restriction enzyme KpnI were added to react at 37° C. for 2 hrs., and then phenol extraction and chloroform extraction were performed followed by ethanol precipitation. The precipitate was dried, which then was dissolved into 50 μl of sterile water. Further, thereto, 1 μl of alkaline phosphatase (from Takara Shuzo), 10 μl of 10× buffer, and 39 μl of sterile water to react at 65° C., and then phenol extraction and chloroform extraction were performed followed by ethanol precipitation. The precipitate was dried, which then was dissolved into sterile water.

(4) Preparation of *E. Coli* Transformants and Selection of Recombinant DNA

*E. coli* strain JM109 was inoculated into 1 ml of an LB medium (1% Bacto tryptone, 0.5% Bacto yeast extract, 0.5% NaCl) to pre-culture at 37° C. for 5 hrs. under aerobic conditions. To 40 ml of an SOB medium (2% Bacto tryptone, 0.5% Bacto yeast extract, 10 mM NaCl, 2.5 mM KCl, 1 mM $MgSO_4$, 1 mM $MgCl_2$), 0.4 ml of this culture was added to culture at 18° C. for 20 hrs. From this culture, cells were harvested by centrifugation, to which then 13 ml of a cool TF solution [20 mM PIPES-KOH (pH 6.0), 200 mM KCl, 10 mM $CaCl_2$, 40 mM $MnCl_2$] was added to stand at 0° C. for 10 min. followed by the second centrifugation. After the supernatant was removed, the precipitated *E. coli* was suspended in 3.2 ml of a cool TF solution, and 0.22 ml of dimethyl sulfoxide was added thereto to stand at 0° C. for 10 min. To 200 μl of the competent cells prepared thereby, 10 μl of the solution containing the recombinant plasmid DNA (the DNA library) prepared in step (3) was added to stand at 0° C. for 30 min., to which then heat shock was given at 42° C. for 30 sec. The cells were cooled at 0° C. for 2 min., to which 1 ml of an SOC medium (20 mM glucose, 2% Bacto tryptone, 0.5% Bacto yeast extract, 10 mM NaCl, 2.5 mM KCl, 1 mM $MgSO_4$, 1 mM $MgCl_2$) was added to culture with shaking at 37° C. for 1 hr. The resulting culture was divided into 200 μl aliquots, each of which was inoculated onto a LBamp medium (a LB medium containing 100 mg/l ampicillin and 1.5% agar) to culture at 37° C. From the colonies of transformants grown on the agar medium, transformants expected to carry the ethylenediamine-N,N'-disuccinate:ethylenediamine lyase gene were selected by colony hybridization. Specifically, the transformants grown on the agar medium were transferred on a nylon membrane (Biodyne A, from Nihon Pall), where microbial cells were lysed, and DNA was fixed. The fixed DNA was treated with the probe (about 300 bp) prepared in step (2) to select colonies having the recombinant DNA of interest by using a DIG Luminescent Detection Kit (from Roche Diagnostics).

(5) Preparation of Recombinant Plasmid

The transformant selected in step (4) was cultured in 100 ml of an LBAmp medium (an LB medium containing 100 mg/L ampicillin) at 37° C. overnight. After cells were harvested, the plasmid DNA was recovered by using a Flexi Prep (from Amersham Biosciences). The resulting recombinant plasmid DNA was named pEDS9001.

Figure 2:
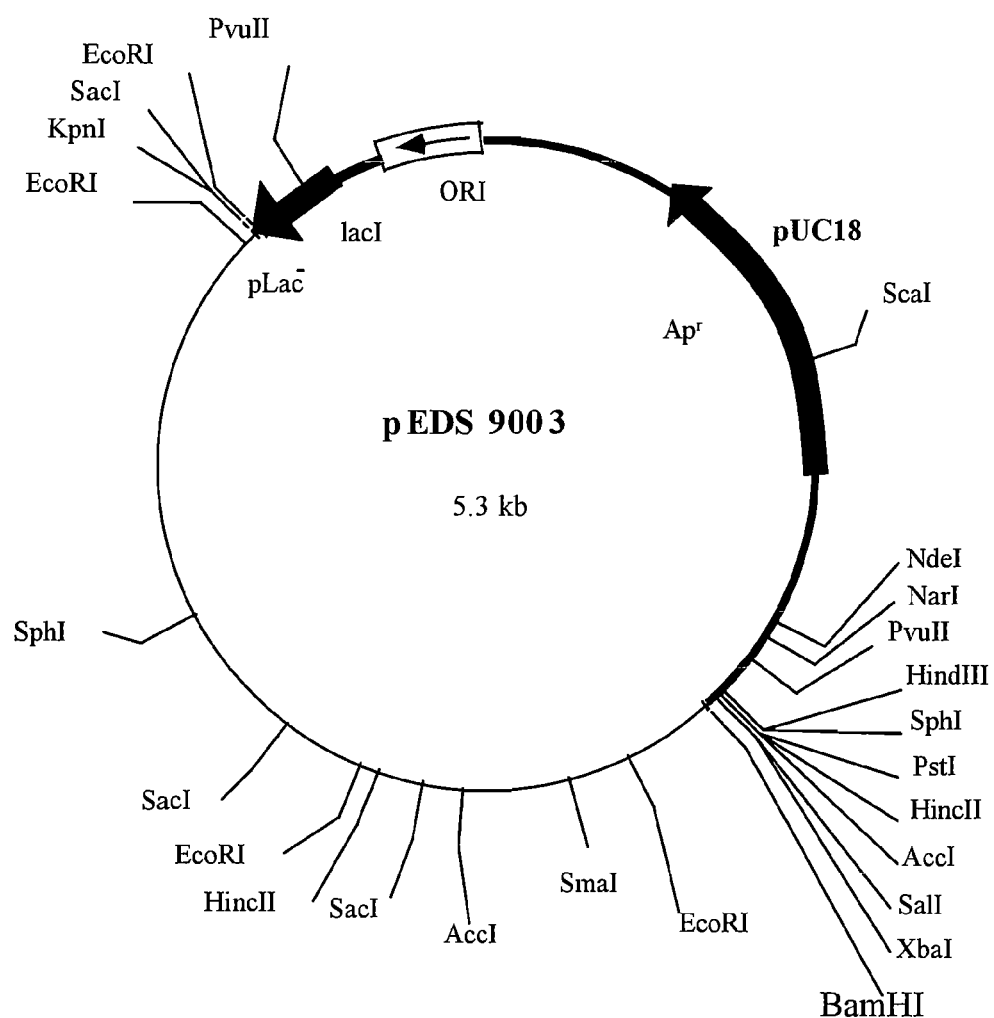
FIG. 2 is a restriction map of the plasmid pEDS9003.

(6) Preparation of Restriction Map and Definition of Ethylenediamine-N,N'-disuccinate:ethylenediamine Lyase Gene Region The plasmid pEDS9001 obtained in step (5) was cleaved by several restriction enzymes to make a restriction map (FIG. 1). In addition, the plasmid was subcloned by an ordinary method. Specifically, after pEDS9001 was cleaved by a restriction enzyme BamHI, agarose gel electrophoresis was performed to extract from the gel a DNA fragment of about 5.3 Kb, which was recovered by using a DNA PREP (from Diatron). After autoligation by using a DNA Ligation Kit Ver. 1 (from Takara Shuzo), *E. coli* strain JM109 was transformed to obtain a plasmid (pEDS9003) (FIG. 2), wherein a fragment of about 2.6 Kb expected to contain the ethylenediamine-N, N'-disuccinate:ethylenediamine lyase gene is inserted.

(7) Determination of Nucleotide Sequence

A nucleotide sequence around the region defined in step (6) was determined by using a fluorescence sequencer ALFII (from Amersham Biosciences). As a result, the nucleotide sequence (SEQ ID NO: 2) encoding an open reading frame made of the amino acid sequence of SEQ ID NO: 1 was discovered.

EXAMPLE 2

Figure 3:
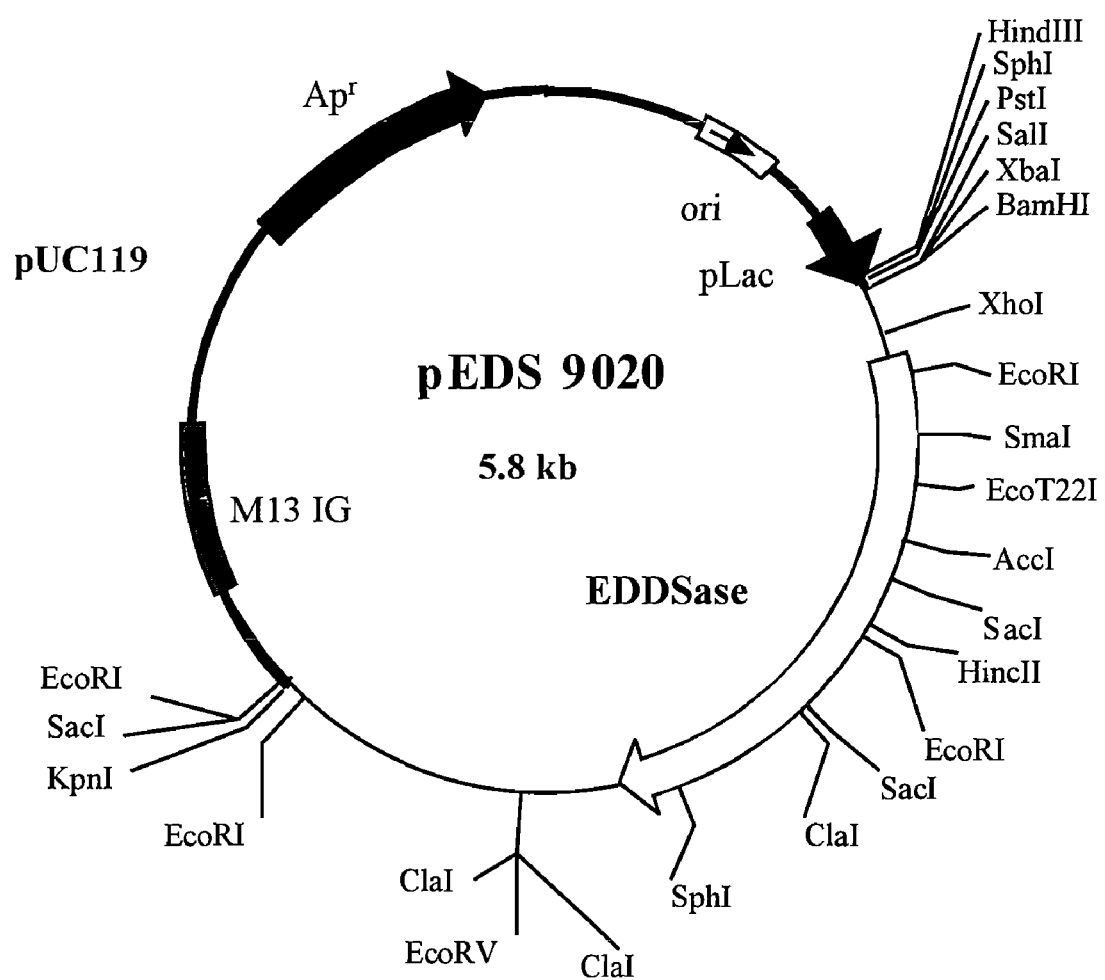
FIG. 3 is a restriction map of the plasmid pEDS9020.

Evaluation of Activity of Transformant wherein Wild Type Ethylenediamine-N,N'-Disuccinate:Ethylenediamine Lyase Gene Derived from MR-E001 Strain is Transferred To 2 μl of the recombinant plasmid pEDS9003 having the ethylenediamine-N,N'-disuccinate:ethylenediamine lyase gene obtained in step (6) of Example 1, 2 μl of 10× buffer for restriction enzyme, 15 μl of sterile water, and 1 μl of the restriction enzyme KpnI were added to react at 37° C. for 2 hrs., and then plasmid DNA was recovered by ethanol precipitation. The plasmid DNA was dried, which then was dissolved into 17 μl of sterile water, 2 μl of 10× buffer for restriction enzyme, and 1 μl of the restriction enzyme BamHI were added to react at 37° C. for 2 hrs. From this reaction solution, a fragment of about 2.6 Kb is prepared by agarose gel electrophoresis, which was inserted into an *E. coli* vector pUC 119. *E. coli* strain JM109 was transformed by using the prepared ligation solution to obtain a plasmid of interest. The thus prepared plasmid was named pEDS9020 (FIG. 3), and the transformant was named JM109/pEDS9020. Each of JM109/pEDS9020 and JM109/pEDS020 [described in JP Patent Publication (Kokai) No. 10-210984A (1998)] as a control was inoculated into 1 ml of an LBAmp medium to culture with shaking at 37° C. for 8 hrs., and then cultured in 40 ml of an LBAmp medium containing 1 mM isopropyl-β-thiogalactoside at 37° C. for 30 hrs. The resulting culture was washed with a 10 mM sodium phosphate buffer solution (pH 8.0), and then was suspended in 2 ml of the buffer solution. A part of the resulting cell suspension was suspended in 50 ml of an aqueous solution, pH of which was 8.0, containing 342 mM fumaric acid and 171 mM ethylenediamine to react at 30° C. A part (0.1 ml) of the reaction mixture was sampled at intervals, and was added into 0.9 ml of a 0.42 N NaOH aqueous solution to stop the reaction. After the cells were removed by centrifugation, S,S-ethylenediamine-N,N'-disuccinate generated thereby was analyzed by using HPLC {WAKOSIL5C8 (from Wako Pure Chemical) [the eluate: 50 mM phosphoric acid containing 10 mM tetra-n-butyl ammonium hydroxide and 0.4 mM $CuSO_4$; pH2]}. One enzyme unit (U) was defined as the amount of enzyme to produce 1 μmol of S,S-ethylenediamine-N,N'-disuccinate per minute under the above determination conditions. The activities of JM109/pEDS9020 and JM109/pEDS020 per cell (per OD630) were determined to be 1.22 mU/ODml and 0.89 mU/ODml, respectively. It was confirmed that the ethylenediamine-N,N'-disuccinate:ethylenediamine lyase derived from the MR-E001 strain has a high activity of the enzyme. Moreover, pEDS9020 was deposited on Feb. 5, 2003, with International Patent Organism Depositary, National Institute of Advanced Industrial Science and Technology (Tsukuba Central 6, 1-1-1 Higashi, Tsukuba, Ibaraki, Japan), under the Accession No. FERM BP-08676.

EXAMPLE 3

Preparation of Modified Ethylenediamine-N,N'-Disuccinate:Ethylenediamine Lyase Genes (1) Induction of Mutations into the Wild Type Ethylenediamine-N,N'-Disuccinate:Ethylenediamine Lyase Gene By using the plasmid pEDS9020 obtained in Example 2, mutations were induced on a random basis into the wild type ethylenediamine-N,N'-disuccinate:ethylenediamine lyase gene. For inducing mutations, utilized was base substitution by nucleotide misincorporation by PCR. The oligonucleotide ED-01 (SEQ ID NO: 5), which contains the initiation codon region of the ethylenediamine-N,N'-disuccinate:ethylenediamine lyase gene, and the oligonucleotide ED-02 (SEQ ID NO: 6), which contains the downstream region by about 50 bp from the termination codon of the gene, were primers for PCR inducing mutations, and 100 μl of a PCR reaction solution having a composition described below was prepared:

Primer:

(SEQ ID NO: 5)
ED-01: CG<u>CCATGG</u>CC CCGCATAACC CAGATGCCAC C (The underlined part is a cleavage recognition site by the restriction enzyme NcoI); and (SEQ ID NO: 6)
ED-02: AAAC<u>AAGCTT</u> CGTCATGGCT ATCCCCTC (The underlined part is a cleavage recognition site by the restriction enzyme HindIII). Composition of reaction solution:

| Template DNA (pEDS9020 prepared in the above step) | 1 μl |
| --- | --- |
| 10× PCR buffer (from GIBCO) | 10 μl |
| 50 mM $MgCl_2$ (from GIBCO) | 3 μl |
| Primer ED-01 | 1 μl |
| Primer ED-02 | 1 μl |
| 2.5 mM dNTP | 2 μl each |
| 10 mM dITP | 2 μl |
| 10 mM dBraUTP | 2 μl |
| Sterile water | 71 μl |
| Taq DNA polymerase (from GIBCO) | 1 μl. |

The above reaction solution was incubated at 94° C. for 30 sec. (denaturation), and at 68° C. for 180 sec. (annealing and extension) for 30 cycles. After the above PCR was completed, an amplified fragment of about 1.5 kb was detected from 10 μl of the reaction solution by using 0.7% agarose gel electrophoresis. In addition, the wild type ethylenediamine-N,N'-disuccinate:ethylenediamine lyase gene was amplified by usual PCR to use it as a control for evaluating heat resistance. Specifically, 100 μl of a PCR reaction solution having a composition described below was prepared:

| Template DNA (pEDS9020) | 1 μl |
| --- | --- |
| 10× Pyrobest Buffer (from Takara Shuzo) | 10 μl |
| Primer ED-01 | 1 μl |
| Primer ED-02 | 1 μl |
| 5 mM dNTP | 2 μl each |
| Sterile water | 78 μl |
| Pyrobest ™ DNA polymerase (from Takara Shuzo) | 1 μl. |

The above reaction solution was incubated at 94° C. for 30 sec. (denaturation), and at 68° C. for 180 sec. (annealing and extension) for 30 cycles. After the above PCR was completed, an amplified fragment of about 1.5 kb was detected from 10 μl of the reaction solution by using 0.7% agarose gel electrophoresis.

In Primer ED-01 and Primer ED-02, the cleavage recognition site by the restriction enzyme NcoI, and the cleavage recognition site by the restriction enzyme HindIII were transferred, respectively (the underlined parts of the nucleotide sequences of Primer ED-01 and Primer ED-02). The amplified DNA product can be readily inserted, by the cleavage thereof using both of the restriction enzymes, into between the NcoI site and the HindIII of an expression vector pFY529V, which will be described later.

(2) Construction of Expression Vector

Figure 4:
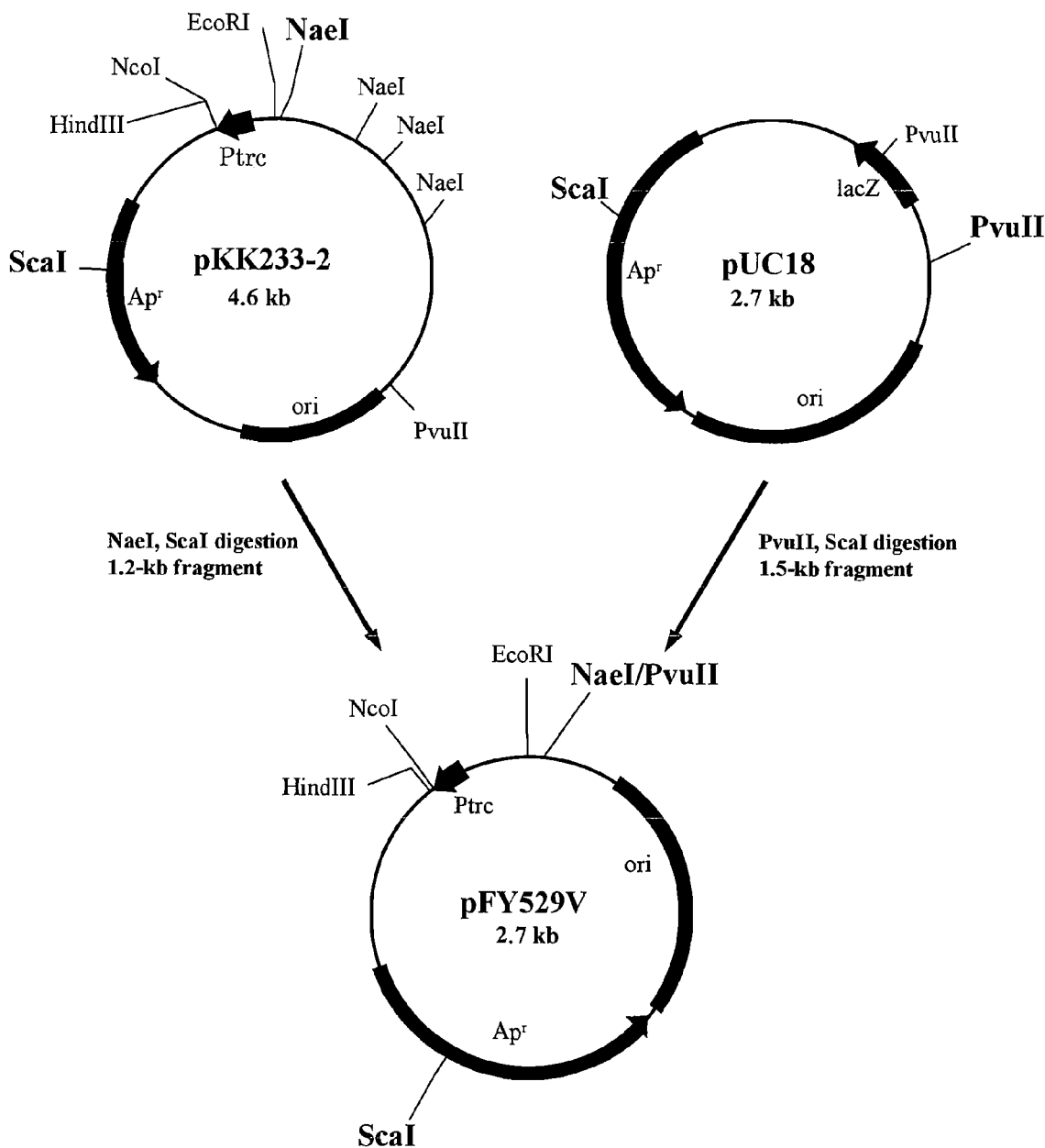
FIG. 4 is an assembly scheme of the expression vector pFY529V.

In order to efficiently detect a remaining ethylenediamine-N,N'-disuccinate:ethylenediamine lyase activity after heat treatment in a screening step, which will be described later, an E. coli expression vector pFY529V, which has a high copy number and great expression efficiency, was prepared (FIG. 4). To 5 μl of an expression vector pKK233-2 having a trc promoter (from Amersham), 1 μl of a restriction enzyme NaeI, 1 μl of a restriction enzyme ScaI, 1 μl of 10× buffer for restriction digestion, and 2 μl of sterile water were added to perform cleavage reaction at 37° C. for 12 hrs. After the cleavage, an NaeI-ScaI fragment (1.2 kb) that does not contain the replication origin of the plasmid was extracted by 0.7% agarose gel electrophoresis, and 3 μl of a TE solution (10 mM Tris, 1 mM EDTA, pH 8.0) containing the DNA fragment was recovered by using a DNA PREP (from Diatron). In tandem with this procedure, to 2 μl of a vector pUC18 having a high copy number, 1 μl of a restriction enzyme PvuII, 1 μl of a restriction enzyme ScaI, 1 μl of 10× buffer for restriction digestion, and 5 μl of sterile water were added to perform cleavage reaction at 37° C. for 12 hrs. After the cleavage, a PvuII-ScaI fragment (1.6 kb) that contains the replication origin of the plasmid was extracted by 0.7% agarose gel electrophoresis, and 1 μl of a TE solution containing the DNA fragment was recovered by using a DNA PREP (from Diatron). Both of the resulting DNA fragments were ligated by using a DNA Ligation Kit Ver. 1 (from Takara Shuzo). By admixing 3 μl of a solution of the NaeI-ScaI fragment from pKK233-2, 1 μl of a solution of the PvuII-ScaI fragment from pUC18, 16 μl of an A solution of the kit, and 4 μl of a B solution of the kit, the ligation was performed at 16° C. for 16 hrs. By using a reaction solution after the ligation, E. coli JM109 strain was transformed by the method described in Example 1 (4). Inoculated was about 10 clones from the resulting transformant colony into 1.5 ml of an LBAmp medium, and incubated with shaking at 37° C. for 12 hrs. After the incubation, cells were harvested from the culture by centrifugation followed by the extraction of the plasmid DNA by using a Flexi Prep (from Amersham Biosciences). After the resulting plasmid DNA was cleaved by the restriction enzyme ScaI, a clone wherein the NaeI-ScaI fragment (1.2 kb) from pKK233-2 and the PvuII-ScaI fragment (1.6 kb) from pUC18 were correctly ligated was selected by 0.7% agarose gel electrophoresis, which was named pFY529V, to use as an expression vector for a mutation library.

(3) Preparation of Mutation Library

A reaction solution containing the ethylenediamine-N,N'-disuccinate:ethylenediamine lyase genes wherein the mutations were induced that was obtained by PCR in step (1) was purified by ethanol precipitation according to the conventional method, and a precipitate was again suspended in 70 µl of sterile water. Thereto, 10 µl of 10× buffer for restriction digestion, 10 µl of a restriction enzyme NcoI, and 10 µl of a restriction enzyme HindIII were added to perform cleavage reaction at 37° C. for 12 hrs. After the cleavage reaction, phenol extraction and chloroform extraction were conducted followed by ethanol precipitation. The precipitate was again suspended in 100 µl of sterile water to obtain a mutated DNA fragment solution. In tandem with this procedure, to 3 µl of the expression vector pFY529V prepared in step (2), 67 µl of sterile water, 10 µl of 10× buffer for restriction digestion, 10 µl of a restriction enzyme NcoI, and 10 µl of a restriction enzyme HindIII were added to perform cleavage reaction at 37° C. for 12 hrs. After the cleavage, phenol extraction and chloroform extraction were conducted followed by ethanol precipitation for purification. Then, the precipitate was again suspended in 10 µl of sterile water to obtain a cleaved pFY529V solution. The mutated DNA fragments and the expression vector pFY529V were ligated by using a DNA Ligation Kit Ver. 1 (from Takara Shuzo). By admixing 3 µl of the above mutated DNA fragment solution, 1 µl of the above cleaved pFY529V solution, 16 µl of an A solution of the kit, and 4 µl of a B solution of the kit, the ligation was performed at 16° C. for 16 hrs. By using a reaction solution after the ligation, E. coli JM109 strain was transformed by the method described in Example 1 [step (4)] to obtain transformants bearing various mutation induced EDDSase genes. In addition, the similar procedure was performed wherein the wild type ethylenediamine-N,N'-disuccinate:ethylenediamine lyase gene that was amplified in step (1) was used as a fragment for insertion. A plasmid was extracted from the resulting transformant colony, and a nucleotide sequence thereof was confirmed by using a fluorescence sequencer ALF II (from Amersham Biosciences). The result was identical with the nucleotide sequence of the wild type ethylenediamine-N,N'-disuccinate:ethylenediamine lyase (SEQ ID NO: 2) determined in Example 1 [step (7)] {besides the change at the fourth base (A→G) due to the transferred NcoI site in Primer ED-01}. This plasmid was named pEDTrc9003, and E. coli containing the plasmid, i.e., JM109/pEDTrc9003, was used as a control in step (4) of screening for an ethylenediamine-N,N'-disuccinate:ethylenediamine lyase with improved heat resistance, which will be described later. Moreover, pEDTrc9003 was deposited on Feb. 5, 2003, with International Patent Organism Depositary, National Institute of Advanced Industrial Science and Technology (Tsukuba Central 6, 1-1-1 Higashi, Tsukuba, Ibaraki, Japan), under the Accession No. FERM BP-08675.

(4) Screening for Ethylenediamine-N,N'-Disuccinate:Ethylenediamine Lyase with Improved Heat Resistance The JM109 transformants containing the mutated ethylenediamine-N,N'-disuccinate:ethylenediamine lyase genes obtained in step (3), and JM109/pEDTrc9003 as a control were inoculated into an LBAmp medium, which had been dispensed in a 48-hole multi-dish in a 1.5 ml aliquot, for liquid culture at 37° C. for 12 hrs. The resulting culture was treated by heat at 50° C. for 30 min. followed by the determination of remaining ethylenediamine-N,N'-disuccinate:ethylenediamine lyase activity according to the method described in Example 2. About 10,000 strains of the transformants obtained in step (3) were screened. As a result, four strains wherein the enzyme activity remained were obtained, whereas the activity was already completely lost in JM109/pEDTrc9003 bearing the wild type ethylenediamine-N,N'-disuccinate:ethylenediamine lyase.

(5) Identification of Mutations

The ethylenediamine-N,N'-disuccinate:ethylenediamine lyase genes wherein the mutations were induced contained in the four candidate strains with improved heat resistance that were obtained in step (4) were analyzed in order to confirm what type of and where the mutation was induced according to the procedure described below. Recombinant plasmid DNAs contained in the four candidate strains with improved heat resistance were purified by using a Flexi Prep (from Amersham Biosciences), and the resulting recombinant plasmid DNAs were named pEDTrcI-2, pEDTrcI-23, pEDTrcJ-05, and pEDTrcK-01, respectively. In addition, mutated enzymes themselves contained in the respective plasmids were named I-2, I-23, J-05, and K-01. Nucleotide sequences of the mutated ethylenediamine-N,N'-disuccinate:ethylenediamine lyase genes contained in these recombinant plasmid DNAs were determined by using a fluorescence sequencer ALF II (from Amersham Biosciences). When the determined nucleotide sequence of each of the mutated ethylenediamine-N,N'-disuccinate:ethylenediamine lyase genes and the nucleotide sequence of the wild type ethylenediamine-N,N'-disuccinate:ethylenediamine lyase (SEQ ID NO: 2) were compared, it was shown that in pEDTrcI-2, the isoleucine residue (ATC) at 166 was substituted with threonine (ACC); in pEDTrcI-23, the lysine residue (AAA) at 120 was substituted with glutamic acid (GAA); in pEDTrcJ-05, the isoleucine residue (ATC) at 166 was substituted with serine (AGC); and in pEDTrcK-01, the alanine residue (GCC) at 365 was substituted with valine (GTC), each of the recombinant plasmid DNAs being a single mutant [the change in nucleotide sequence encoding each of the amino acids is indicated in (- - -)].

(6) Evaluation of Heat Resistance of Single Mutants

Heat resistance of the four single mutants of the ethylenediamine-N,N'-disuccinate:ethylenediamine lyase (I-2, I-23, J-05, and K-01), which were identified in step (5), was evaluated more thoroughly. Four E. coli strains bearing the single mutants of the ethylenediamine-N,N'-disuccinate:ethylenediamine lyase (JM109/pEDTrcI-2, JM109/pEDTrcI-23, JM109/pEDTrcJ-05, and JM109/pEDTrck-01), and E. coli bearing the wild type ethylenediamine-N,N'-disuccinate:ethylenediamine lyase JM109/pEDTrc9003 were inoculated into 1.5 ml of an LBAmp medium to incubate with shaking at 30° C. for 8 hrs. Then, 400 µl of each of the culture solutions was inoculated into 40 ml of an LBAmp medium prepared in a 500 ml Erlenmeyer's flask to culture with shaking at 37° C. for 12 hrs. Collected was 1.5 ml of the resulting culture and cells were harvested by centrifugation followed by washing with a 50 mM boric acid buffer solution (pH 9.0). Then, the cells were suspended in 1.5 ml of the buffer solution to prepare a cell suspension. This cell suspension was sonicated to destruct the cells and obtain crude enzyme extract. The resulting crude extract was subjected to heat treatment for 30 min. at 40, 45, 50, 55, 60, and 65° C., and then immediately cooled to 4° C. After the heat treatment, the ethylenediamine-N,N'-disuccinate:ethylenediamine lyase activity was measured according to the method described in Example 2. For each mutant, the relative remaining activity to the control (100%), which was kept cooled at 4° C. without heat treatment, was determined.

Figure 5:
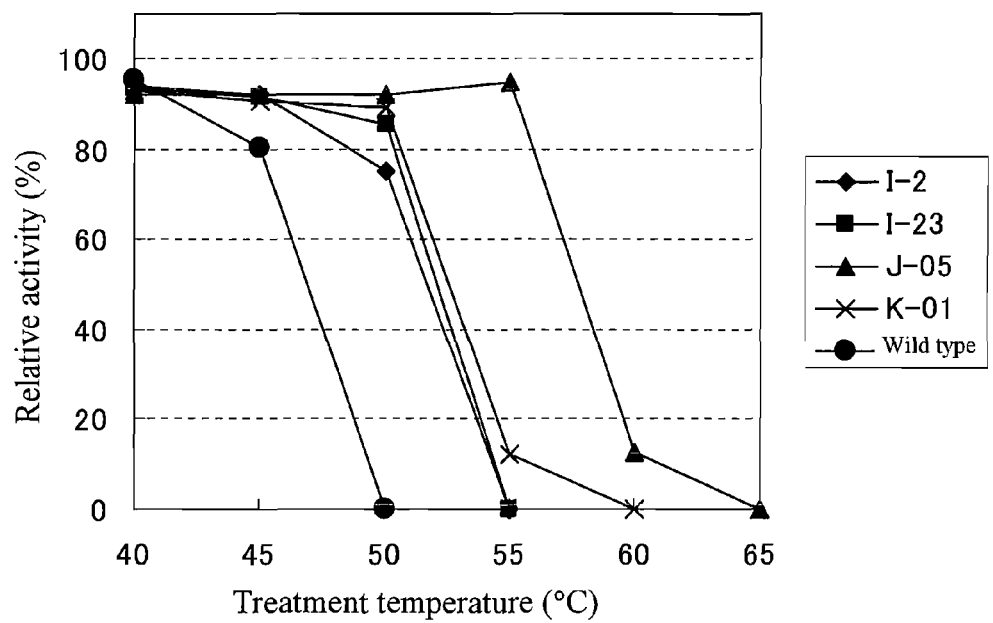
FIG. 5 is a graph for evaluating heat resistance of the single mutants.

The results are shown in FIG. 5. In FIG. 5, the vertical axis represents a remaining ethylenediamine-N,N'-disuccinate:ethylenediamine lyase activity, and the horizontal axis represents a treatment temperature. The wild type ethylenediamine-N,N'-disuccinate:ethylenediamine lyase completely lost its enzyme activity at 50° C. On the other hand, the single mutants, I-2, I-23, J-05, and K-01, retained the relative remaining activities of 75% at 50° C., 85% at 50° C., 12% at 60° C., and 12% at 55° C., respectively, and it was confirmed that the heat resistance of these single mutants improved compared with that of the wild type.

EXAMPLE 4

Figure 6:
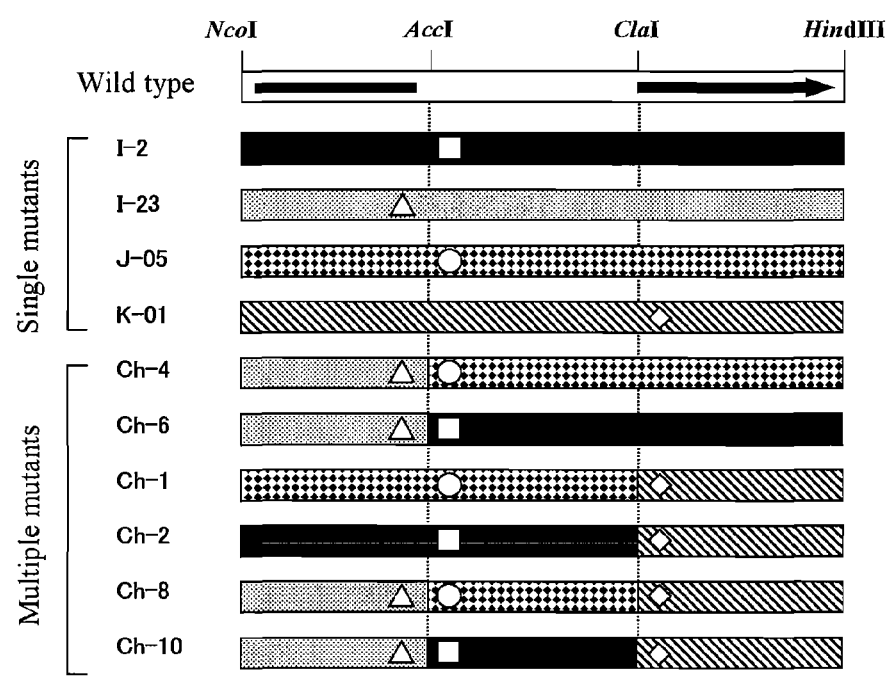
FIG. 6 is a schematic representation to illustrate the constructions of the single mutants and the multiple mutants: square indicates the mutations of T497C (Ile166Thr), triangle indicates the mutations of A358G (Lys120Glu), circle indicate the mutations of T497G (Ile166Ser), and diamond indicates the mutations of C1094T (Ala365Val), respectively.

Preparation of Multiple Mutants and Evaluation of Heat Resistance Thereof (1) Preparation of Multiple Mutants Multiple mutants were prepared by combining the amino acid substitutions in the four single mutants whose improved heat resistance was confirmed in Example 3. The mutation sites of the single mutants, I-2, I-23, J-05, and K-01, were the isoleucine residue at 166, the lysine residue at 120, the isoleucine residue at 166, and the alanine residue at 366, respectively. By cleaving the ethylenediamine-N,N'-disuccinate:ethylenediamine lyase gene DNA fragment by restriction enzymes EcoT22I, AccI, and ClaI, provided were DNA fragments, each of which contains one of these mutation sites (FIG. 6). By allowing the cleaved DNA fragment of a single mutant to replace the corresponding DNA fragment derived from a different single mutant and religate it, a chimeric enzyme gene having double mutation or triple mutation was formed (FIG. 6). For example, for preparing a double mutant, Ch-4, first, pEDTrcI-23 that contained a gene encoding the single mutant I-23 was cleaved by restriction enzymes NcoI and AccI, and the shorter fragment (about 0.5 kb) of the resulting DNA fragments was extracted by agarose gel electrophoresis. In tandem with this procedure, pEDTrcJ-05 that contained a gene encoding the single mutant J-05 was cleaved by restriction enzymes NcoI and AccI, and the longer fragment (about 3.8 kb including the vector) of the resulting DNA fragments was extracted by agarose gel electrophoresis. Both of the DNA fragments were recovered by using a DNA PREP (from Diatron) and ligated by using a DNA Ligation Kit Ver. 1 (from Takara Shuzo), and then E. coli JM109 was transformed therewith according to the conventional method. From the resulting transformant, a plasmid was extracted and cleaved by restriction enzymes NcoI and AccI to confirm that the ligation was correct by agarose gel electrophoresis. This plasmid DNA and the chimeric enzyme were named pEDTrcCh-4 and Ch-4, respectively. Likewise, an NcoI-AccI fragment (about 0.5 kb) from the single mutant I-23 and an NcoI-AccI fragment (about 3.8 kb including the vector) from the single mutant I-2 were ligated to prepare plasmid DNA pEDTrcCh-6 and a chimeric enzyme Ch-6. According to the similar procedure, an NcoI-ClaI fragment (about 1 kb) from the single mutant J-05 and an NcoI-ClaI fragment (about 3.3 kb including the vector) from the single mutant K-01 were ligated to prepare plasmid DNA pEDTrcCh-1 and a chimeric enzyme Ch-1. An NcoI-ClaI fragment (about 1 kb) from the single mutant I-2 and an NcoI-ClaI fragment (about 3.3 kb including the vector) from the single mutant K-01 were ligated to prepare plasmid DNA pEDTrcCh-2 and a chimeric enzyme Ch-2. Further, for preparing triple mutants, an NcoI-AccI fragment (about 0.5 kb) from the single mutant 1-23 and an AccI-ClaI fragment (about 0.5 kb) from the single mutant J-05, and an NcoI-ClaI fragment (about 3.3 kb including the vector) from the single mutant K-01 are ligated to prepare plasmid DNA pEDTrcCh-8 and a chimeric enzyme Ch-8. An NcoI-AccI fragment (about 0.5 kb) from the single mutant I-23 and an AccI-ClaI fragment (about 0.5 kb) from the single mutant I-2, and an NcoI-ClaI fragment (about 3.3 kb including the vector) from the single mutant K-01 are ligated to prepare plasmid DNA pEDTrcCh-10 and a chimeric enzyme Ch-10. The structures of the resulting chimeric enzymes are shown in FIG. 6.

(2) Evaluation of Heat Resistance of Multiple Mutants

Figure 7:
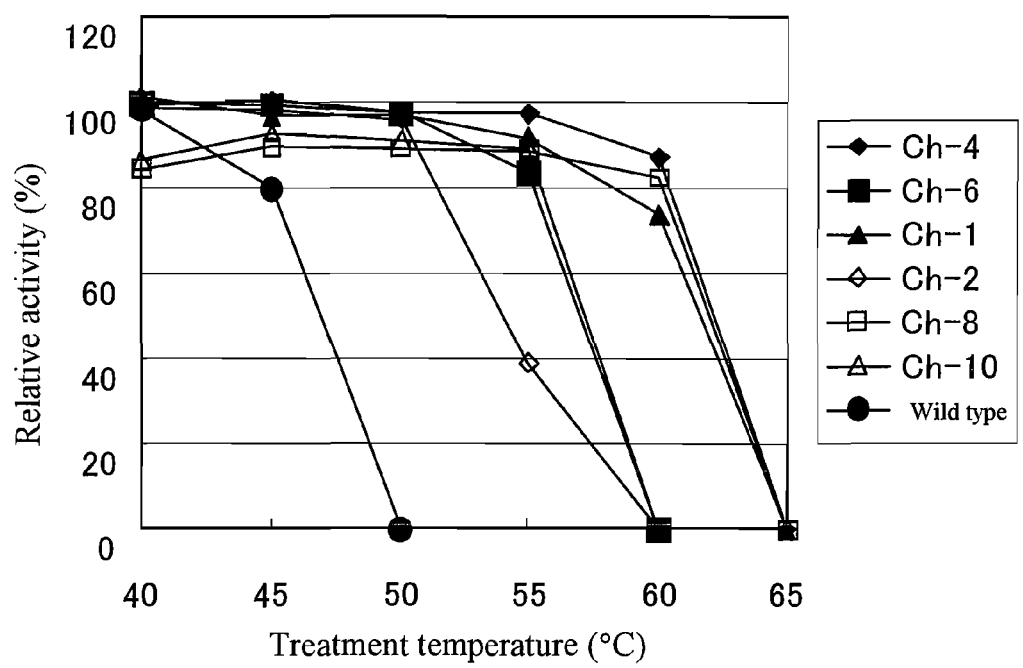
FIG. 7 is a graph for evaluating heat resistance of the multiple mutants.

Heat resistance of the six multiple mutants of the ethylenediamine-N,N'-disuccinate:ethylenediamine lyase (Ch-4, Ch-6, Ch-1, Ch-2, Ch-8, and Ch-10), which were prepared in step (1), was evaluated. Six E. coli strains bearing the multiple mutants of the ethylenediamine-N,N'-disuccinate:ethylenediamine lyase (JM109/pEDTrcCh-4, JM109/pEDTrcCh-6, JM109/pEDTrcCh-1, JM109/pEDTrcCh-2, JM109/pEDTrcCh-8, and JM109/pEDTrcCh-10), and E. coli bearing the wild type ethylenediamine-N,N'-disuccinate:ethylenediamine lyase JM109/pEDTrc9003 were inoculated into 1.5 ml of an LBAmp medium to incubate with shaking at 30° C. for 8 hrs. Then, 400 µl of each of the culture solutions was inoculated into 40 ml of an LBAmp medium prepared in a 500 ml Erlenmeyer's flask to culture with shaking at 37° C. for 12 hrs. Collected was 1.5 ml of the resulting culture and cells were harvested by centrifugation followed by washing with a 50 mM boric acid buffer solution (pH 9.0). Then, the cells were suspended in 1.5 ml of the buffer solution to prepare a cell suspension. This cell suspension was sonicated to destruct the cells and obtain a crude enzyme extract. The resulting crude extract was subjected to heat treatment for 30 min. at 40, 45, 50, 55, 60, and 65° C., and then immediately cooled to 4° C. After the heat treatment, the ethylenediamine-N,N'-disuccinate:ethylenediamine lyase activity was measured according to the method described in Example 2. For each mutant, the relative remaining activity to the control, which was kept cooled at 4° C. without heat treatment, was determined. The results are shown in FIG. 7. In FIG. 7, the vertical axis represents a remaining ethylenediamine-N,N'-disuccinate:ethylenediamine lyase activity, and the horizontal axis represents a treatment temperature. The wild type ethylenediamine-N,N'-disuccinate:ethylenediamine lyase completely lost its enzyme activity at 50° C. On the other hand, the multiple mutants, Ch-4, Ch-6, Ch-1, Ch-2, Ch-8, and Ch-10, retained the relative remaining activities of 72% at 60° C., 89% at 55° C., 56% at 60° C., 25% at 55° C., 90% at 60° C., and 97% at 55° C., respectively, and it was confirmed that the heat resistance of these multiple mutants improved compared with that of the wild type and the single mutants.

All references, articles, publications, patents, and patent applications cited herein are hereby incorporated by reference in their entireties.

INDUSTRIAL APPLICABILITY

The present invention provides a nucleotide sequence and an amino acid sequence of a wild type ethylenediamine-N,N'-disuccinate:ethylenediamine lyase derived from *Brevundimonas diminuta* strain MR-E001. Further, the present invention provides a nucleotide sequence and an amino acid sequence of a modified ethylenediamine-N,N'-disuccinate:ethylenediamine lyase derived from the wild type ethylenediamine-N,N'-disuccinate:ethylenediamine lyase. Moreover, the present invention provides recombinant DNAs containing the wild type and the modified ethylenediamine-N,N'-disuccinate:ethylenediamine lyase genes; transformants or transductants containing the recombinant DNAs; and a method of preparing diaminoalkylene-N,N'-disuccinates by using the transformants or transductants. By the present invention, diaminoalkylene-N,N'-disuccinates can be prepared efficiently.

Sequence Table Free Text
  SEQ ID NO: 1: Xaa represents Met or deletion
  SEQ ID NO: 3: Artificial DNA
  SEQ ID NO: 4: Artificial DNA
  SEQ ID NO: 5: Artificial DNA
  SEQ ID NO: 6: Artificial DNA

The invention claimed is:

1. An isolated protein comprising the amino acid sequence of SEQ ID NO: 1, and having an ethylenediamine-N,N'-disuccinate:ethylenediamine lyase activity.

2. An isolated protein comprising the amino acid sequence of SEQ ID NO:1 having 1 to 10 substitutions, wherein one substitution is the substitution of the lysine residue at position 120 with a glutamic acid residue, and wherein said protein has ethylenediamine-N,N'-disuccinate:ethylenediamine lyase activity that is heat resistant.

3. An isolated protein comprising the amino acid sequence of SEQ ID NO:1 having 1 to 10 substitutions, wherein one substitution is the substitution of the isoleucine residue at position 166 with a serine residue, and wherein said protein has ethylenediamine-N,N'-disuccinate:ethylenediamine lyase activity that is heat resistant.

4. An isolated protein comprising the amino acid sequence of SEQ ID NO:1 having 1 to 10 substitutions, wherein one substitution is the substitution of the isoleucine residue at position 166 with a threonine residue, and wherein said protein has ethylenediamine-N,N'-disuccinate:ethylenediamine lyase activity that is heat resistant.

5. An isolated protein comprising the amino acid sequence of SEQ ID NO:1 having 1 to 10 substitutions, wherein one substitution is the substitution of the alanine residue at position 365 with a valine residue, and wherein said protein has ethylenediamine-N,N'-disuccinate:ethylenediamine lyase activity that is heat resistant.

6. An isolated protein comprising the amino acid sequence of SEQ ID NO:1 having 2 to 10 substitutions, wherein said substitutions include the substitution of the lysine residue at position 120 with a glutamic acid residue and the substitution of the isoleucine residue at position 166 with a serine residue, and wherein said protein has ethylenediamine-N,N'-disuccinate:ethylenediamine lyase activity that is heat resistant.

7. An isolated protein comprising the amino acid sequence of SEQ ID NO:1 having 2 to 10 substitutions, wherein said substitutions include the substitution of the lysine residue at position 120 with a glutamic acid residue and the substitution of the isoleucine residue at position 166 with a threonine residue and wherein said protein has ethylenediamine-N,N'-disuccinate:ethylenediamine lyase activity that is heat resistant.

8. An isolated protein comprising the amino acid sequence of SEQ ID NO:1 having 2 to 10 substitutions, wherein said substitutions include the substitution of the isoleucine residue at position 166 with a serine residue, and the substitution of the alanine residue at position 365 with a valine residue, and wherein said protein has ethylenediamine-N,N'-disuccinate:ethylenediamine lyase activity that is heat resistant.

9. An isolated protein comprising the amino acid sequence of SEQ ID NO:1 having 2 to 10 substitutions, wherein said substitutions include the substitution of the isoleucine residue at position 166 with a threonine residue, and the substitution of the alanine residue at position 365 with a valine residue, and wherein said protein has ethylenediamine-N,N'-disuccinate:ethylenediamine lyase activity that is heat resistant.

10. An isolated protein comprising the amino acid sequence of SEQ ID NO:1 having 3 to 10 substitutions, wherein said substitutions include the substitution of the lysine residue at position 120 with a glutamic acid residue, and the substitution of the isoleucine residue at position 166 with a serine residue and the substitution of the alanine residue at position 365 with a valine residue, and wherein said protein has ethylenediamine-N,N'-disuccinate:ethylenediamine lyase activity that is heat resistant.

11. An isolated protein comprising the amino acid sequence of SEQ ID NO:1 having 3 to 10 substitutions, wherein said substitutions include the substitution of the lysine residue at position 120 with a glutamic acid residue and the substitution of the isoleucine residue at position 166 with a threonine residue and the substitution of the alanine residue at position 365 with a valine residue, and wherein said protein has ethylenediamine-N,N'-disuccinate:ethylenediamine lyase activity that is heat resistant.

12. The isolated protein according to claim 2, wherein the ethylenediamine-N,N'-disuccinate:ethylenediamine lyase retains its activity in the temperature range of 45° C. to 60° C.

* * * * *